(12) United States Patent
Dai et al.

(10) Patent No.: US 12,089,923 B2
(45) Date of Patent: Sep. 17, 2024

(54) SCANNING CONTROL SYSTEM AND METHOD FOR MAGNETIC RESONANCE IMAGING SYSTEM

(71) Applicant: GE Precision Healthcare LLC, Waukesha, WI (US)

(72) Inventors: Qingyu Dai, Beijing (CN); Yanting Huo, Beijing (CN); Jiabin Yao, Beijing (CN); Saban Kurucay, Waukesha, WI (US); Jonathan C West, Waukesha, WI (US); Yuwen Li, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 18/387,197

(22) Filed: Nov. 6, 2023

(65) Prior Publication Data

US 2024/0065571 A1 Feb. 29, 2024

Related U.S. Application Data

(62) Division of application No. 16/951,538, filed on Nov. 18, 2020, now Pat. No. 11,844,599.

(30) Foreign Application Priority Data

Nov. 25, 2019 (CN) .......................... 201911167131.8

(51) Int. Cl.
| | | |
|---|---|---|
| *A61B 5/055* | (2006.01) | |
| *G01R 33/3415* | (2006.01) | |
| *G01R 33/48* | (2006.01) | |
| *G01R 33/54* | (2006.01) | |

(52) U.S. Cl.
CPC .......... *A61B 5/055* (2013.01); *G01R 33/3415* (2013.01); *G01R 33/4822* (2013.01); *G01R 33/543* (2013.01)

(58) Field of Classification Search
CPC .. A61B 5/055; A61B 5/70; A61B 5/74; A61B 5/0064; G01R 33/3415; G01R 33/4822; G01R 33/543; G01R 33/283; G01R 33/288; G01R 33/3664; G01R 33/3628
See application file for complete search history.

(56) References Cited

U.S. PATENT DOCUMENTS

| | | | |
|---|---|---|---|
| 6,912,415 | B2 | 6/2005 | Kruger et al. |
| 6,975,113 | B1 | 12/2005 | Gurr |
| 7,346,383 | B2 | 3/2008 | Riederer et al. |
| 7,738,944 | B2 | 6/2010 | Ho et al. |

(Continued)

FOREIGN PATENT DOCUMENTS

CN 109965878 7/2019

*Primary Examiner* — Patrick Fernandes
*Assistant Examiner* — Nicholas A Robinson
(74) *Attorney, Agent, or Firm* — Fletcher Yoder P.C.

(57) ABSTRACT

An embodiment of the present invention provides a scanning control system for a magnetic resonance imaging system, comprising: a first 3D camera, configured to capture a three-dimensional image of a scan subject located on a scanning table of the magnetic resonance imaging system; a processing device, configured to identify body position information of the scan subject based on the three-dimensional image; and a control device, configured to set scanning parameters related to a body position based on the body position information.

2 Claims, 18 Drawing Sheets

(56) References Cited

U.S. PATENT DOCUMENTS

| | | |
|---|---|---|
| 9,364,663 B2 | 6/2016 | Doerr et al. |
| 10,739,421 B1 | 8/2020 | Ma et al. |
| 2009/0177076 A1 | 7/2009 | Aldefeld et al. |
| 2011/0201916 A1* | 8/2011 | Duyn .................... A61B 5/721 |
| | | 600/410 |
| 2012/0086449 A1 | 4/2012 | Graesslin et al. |
| 2015/0332498 A1* | 11/2015 | Zhang ................... G06T 11/003 |
| | | 345/420 |
| 2016/0338614 A1 | 11/2016 | Gall et al. |
| 2017/0059678 A1 | 3/2017 | Kannengiesser et al. |
| 2017/0311841 A1* | 11/2017 | Rothgang ............ G01R 33/283 |
| 2017/0350953 A1 | 12/2017 | Huang et al. |
| 2018/0350081 A1* | 12/2018 | Hsieh ..................... G06T 7/248 |
| 2021/0121092 A1 | 4/2021 | Kawajiri et al. |

\* cited by examiner

SCANNING CONTROL SYSTEM AND METHOD FOR MAGNETIC RESONANCE IMAGING SYSTEM

CROSS-REFERENCE TO RELATED APPLICATION

This application claims priority to and the benefit of U.S. patent application Ser. No. 16/951,538, entitled "SCANNING CONTROL SYSTEM AND METHOD FOR MAGNETIC RESONANCE IMAGING SYSTEM", filed Nov. 18, 2020, which claims priority to Chinese Application No. 201911167131.8, filed Nov. 25, 2019, which are herein incorporated by reference in their entirety.

TECHNICAL FIELD

Embodiments disclosed in the present invention relate to medical imaging technologies, and more specifically, to a scanning control system and method for a magnetic resonance imaging system.

BACKGROUND

Magnetic resonance imaging (MRI), as a medical imaging modality, can obtain three-dimensional images of the human body without using X-rays or other ionizing radiation. When a part of interest of a patient is imaged using a magnetic resonance imaging system, the part of interest of the patient needs to be scanned. Before a scanning task is performed, a pre-scanning task needs to be executed to make adequate preparation for formal scanning. For example, it is needed to input patient information, help the patient with positioning, set scanning parameters, optimize the scanning parameters, and so on. For different purposes such as improving image quality, simplifying the operation process, reducing operation time, and increasing patient comfort, it is desired that a more precise and optimized control can be performed on the magnetic resonance imaging system in each process of pre-scanning and scanning as far as possible.

In the prior art, there is still room for optimization in both the pre-scanning process and the scanning process to meet increasing clinical diagnostic requirements. For example, before scanning, it is needed to communicate with a patient many times or move the patient many times to position the patient onto a scanning table at a generally appropriate position; since it is difficult to precisely align a part of interest of the patient with a scanning center, it takes a long time to adjust the position or the image quality is affected; due to improper setting of scanning parameters or improper selection of a coil channel, the image quality is lowered or images cannot be used for lesion check and thus additional scanning is needed.

SUMMARY

One embodiment of the present invention provides a scanning control system for a magnetic resonance imaging system, comprising: a first 3D camera, configured to capture a three-dimensional image of a scan subject located on a scanning table of the magnetic resonance imaging system; a processing device, configured to identify body position information of the scan subject based on the three-dimensional image; and a control device, configured to set scanning parameters related to a body position based on the body position information.

Optionally, the processing device is further configured to determine, based on the body position of the scan subject displayed in the three-dimensional image, a slice position and angle for image reconstruction, and send the determined slice position and angle to an image reconstruction unit of the magnetic resonance imaging system.

Another embodiment of the present invention further provides a scanning control system for a magnetic resonance imaging system, comprising:

a 3D camera, configured to photograph a scanning table of the magnetic resonance imaging system and a scan subject located on the scanning table to obtain a three-dimensional image, wherein the scan subject is coupled to an RF receive coil, and the RF receive coil comprises a plurality of coil units arranged in an array;

a processing device, configured to determine relative position information of a part of interest of the scan subject and the RF receive coil based on the three-dimensional image, and select a coil unit required to be turned on from the RF receive coil based on the determined relative position information; and a control device, configured to turn on the selected coil unit.

Optionally, the RF receive coil comprises a first receive coil disposed in the scanning table and a second receive coil disposed on a body surface of the scan subject; the processing device is further configured to identify, based on the three-dimensional image, a coupling manner in which the second receive coil is coupled to the scan subject, and select all or one of the first receive coil and the second receive coil based on the coupling manner in which the second receive coil is coupled to the scan subject; the control device is configured to turn on the coil selected from the first receive coil and the second receive coil.

Optionally, when the first receive coil is selected, the processing device is configured to select a required coil unit from the first receive coil based on relative position information of the part of interest of the scan subject and the first receive coil; when the second receive coil is selected, the processing device is configured to select a required coil unit from the second receive coil based on relative position information of the part of interest of the scan subject and the second receive coil.

Optionally, the first 3D camera is further configured to photograph a first region to obtain a first environment image before a scanning process starts or after the scanning process ends, wherein the first region comprises a positioning region of the scanning table; the processing device is configured to compare the first environment image with a prestored first standard environment image; the control device is configured to indicate a maintenance state of the magnetic resonance imaging system based on a comparison result of the first environment image and the first standard environment image.

Optionally, the system further comprises a second 3D camera configured to photograph a third region to obtain the third environment image before the scanning process starts or after the scanning process ends, wherein the first 3D camera and the second 3D camera are respectively located on two sides of a magnet assembly of the magnetic resonance imaging system, and the third region comprises a region located outside a scanning chamber of the magnetic resonance imaging system and opposite to a rear end of the scanning chamber; the processing device is further configured to compare the third environment image with a prestored second standard environment image; the control device is further configured to indicate the maintenance state of the magnetic resonance imaging system based on a comparison result of the third environment image and the second standard environment image.

One embodiment of the present invention provides a scanning control method for a magnetic resonance imaging system, comprising:

obtaining a three-dimensional image, captured by a first 3D camera, of a scan subject located on a scanning table of the magnetic resonance imaging system;

identifying body position information of the scan subject based on the three-dimensional image; and setting scanning parameters related to a body position based on the body position information.

Optionally, the method further comprises: determining, based on the body position of the scan subject displayed in the three-dimensional image, a slice position and angle for image reconstruction, and sending the determined slice position and angle to an image reconstruction unit of the magnetic resonance imaging system.

Another embodiment of the present invention provides a scanning control method for a magnetic resonance imaging system, comprising:

obtaining a scanning table of the magnetic resonance imaging system and a scan subject located on the scanning table that are photographed by a first 3D camera to obtain a three-dimensional image, wherein the scan subject is coupled to an RF receive coil, and the RF receive coil comprises a plurality of coil units arranged in an array;

determining relative position information of a part of interest of the scan subject and the RF receive coil based on the three-dimensional image, and selecting a coil unit required to be turned on from the RF receive coil based on the determined relative position information; and turning on the selected coil unit.

Optionally, the RF receive coil comprises a first receive coil disposed in the scanning table and a second receive coil disposed on a body surface of the scan subject, the method further comprising:

identifying, based on the three-dimensional image, a coupling manner in which the second receive coil is coupled to the scan subject, and selecting all or one of the first receive coil and the second receive coil based on the coupling manner in which the second receive coil is coupled to the scan subject; and turning on the coil selected from the first receive coil and the second receive coil.

Optionally, when the first receive coil is selected, a required coil unit is selected from the first receive coil based on relative position information of the part of interest of the scan subject and the first receive coil; when the second receive coil is selected, a required coil unit is selected from the second receive coil based on relative position information of the part of interest of the scan subject and the second receive coil.

Optionally, the method further comprises: obtaining, before a scanning process starts or after the scanning process ends, a first environment image of a first region that is photographed by the first 3D camera, wherein the first region comprises a positioning region of the scanning table; comparing the first environment image with a prestored first standard environment image; and indicating a maintenance state of the magnetic resonance imaging system based on a comparison result of the first environment image and the first standard environment image.

Optionally, the method further comprises: obtaining, before the scanning process starts or after the scanning process ends, a second environment image of a third region that is captured by a second 3D camera, wherein the first 3D camera and the second 3D camera are respectively located on two sides of a magnet assembly of the magnetic resonance imaging system, and the third region comprises a region located outside a scanning chamber of the magnetic resonance imaging system and opposite to a rear end of the scanning chamber; comparing the third environment image with a prestored second standard environment image; and indicating the maintenance state of the magnetic resonance imaging system based on a comparison result of the third environment image and the second standard environment image.

It should be understood that the brief description above is provided to introduce in simplified form some concepts that will be further described in the Detailed Description of the Embodiments. The brief description above is not meant to identify key or essential features of the claimed subject matter. The protection scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present invention will be better understood by reading the following description of non-limiting embodiments with reference to the accompanying drawings, where.

DETAILED DESCRIPTION OF THE EMBODIMENTS

Figure 1:
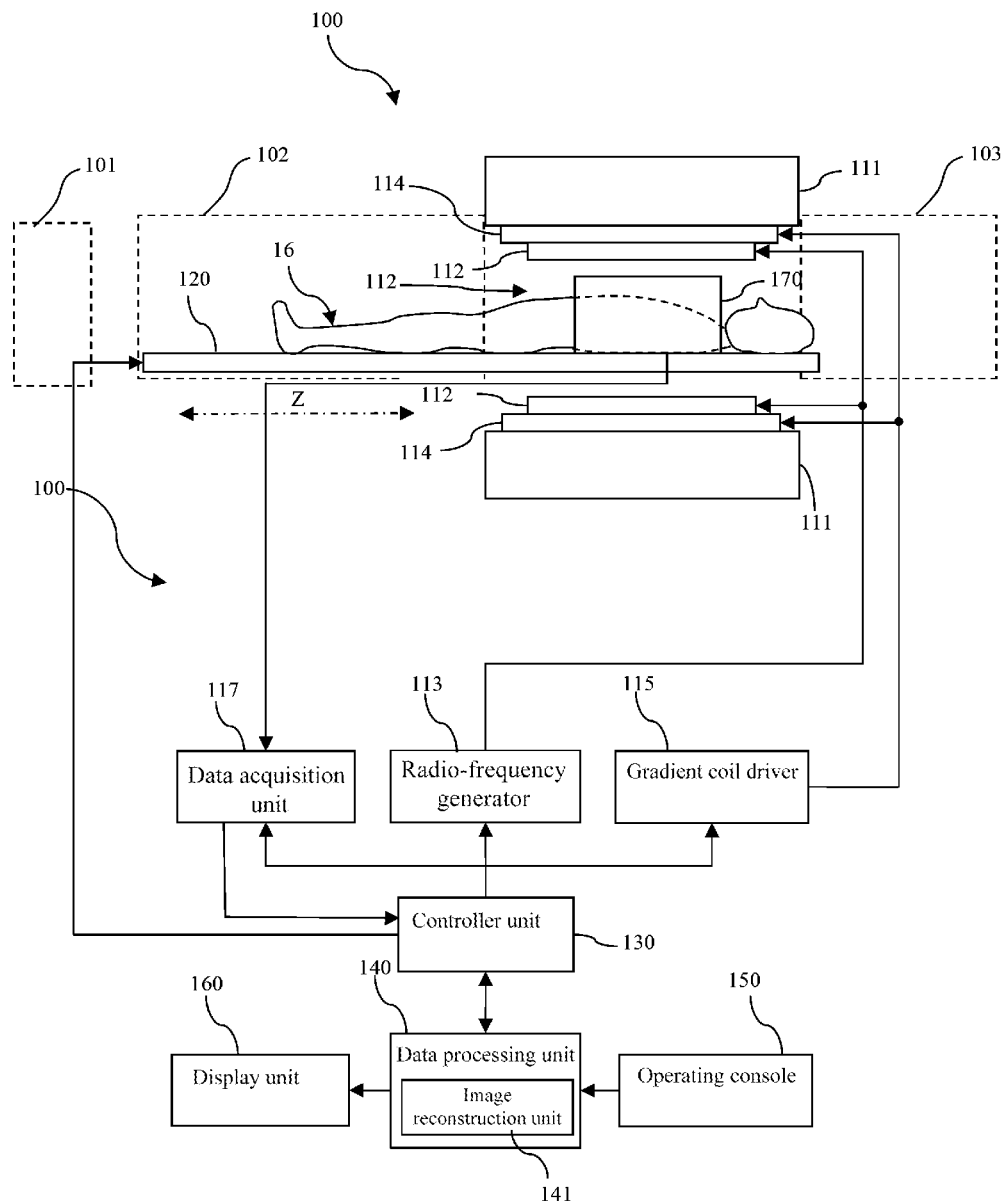
FIG. 1 shows a block diagram of one example of a magnetic resonance imaging system.

Various embodiments described below include a pre-scanning control system and method for a magnetic resonance imaging system. FIG. 1 shows a block diagram of one example of a magnetic resonance imaging system.

As shown in FIG. 1, the magnetic resonance imaging (MRI) system 100 includes a scanner 110, a table 120, a controller unit 130, a data processing unit 140, an operating console 150, and a display unit 160.

In one example, the scanner 110 may include a main magnet assembly 111. The main magnet assembly 111 usually includes an annular superconducting magnet defined in a housing, where the annular superconducting magnet is mounted in an annular vacuum container. The annular superconducting magnet and the housing thereof define a cylindrical space, namely, a scanning chamber 116 shown in FIG. 1, surrounding a scan subject 16. The scanning chamber 116 defines an imaging region of the magnetic resonance imaging system or at least part of the imaging region.

The main magnet assembly 111 is disposed in a scanning room. A first region 101, a second region 102, and a third region 103 may be defined outside the main magnet assembly 111, wherein the first region 101 is located outside the scanning chamber 116. Specifically, the first region 101 may be a region where any scan subject resides before being positioned to the table 120 in the scanning room. The second region 102 may be a region defining the table 120. The third region 103 may be a region located outside the scanning chamber and opposite to a rear end of the scanning chamber. The rear end of the scanning chamber indicates an end opposite to a patient entrance of the scanning chamber. For example, the third region 103 may include a positioning region for a rear axle of the main magnet assembly 111.

The table 120 is used for carrying the scan subject 16, for example, a patient. The table 120 may include a lifting platform (not shown in the figure) and a movable table board disposed on the lifting platform. The table 120 is generally fixed at a front end of the main magnet assembly 111. The movable table board is used for carrying the scan subject 16, and configured to be able to communicate with the patient entrance of the scanning chamber 116, and move along the Z direction to allow the scan subject 16 thereon to enter and exit the scanning chamber 116 or travel in the scanning chamber along the Z direction. That is, the movable table board may move from outside of the imaging region to an imaging position in the imaging region, wherein the imaging position may vary with a part to be imaged. The movable table board may also move step by step between a plurality of imaging positions in the imaging region to perform imaging of a plurality of imaging parts, such as whole body imaging.

The scanner 110 further includes an RF transmit coil 112, a radio-frequency generator 113, a gradient coil assembly 114, a gradient coil driver 115, an RF receive coil 170, and a data acquisition unit 117. When an imaging scanning process is performed on a part of interest of the scan subject 16, the scanner 110 is configured to obtain image data of the scan subject 16.

Specifically, the main magnet assembly 111 generates a constant magnetic field, for example, a static magnetic field B0, in a Z direction of the scanning chamber 116. The MRI system 100 uses the formed static magnetic field B0 to emit a magnetostatic pulse signal to the subject 16 placed in the scanning chamber 116, so that the precession of protons in the body of the subject 16 is ordered to generate a longitudinal magnetization vector.

The radio-frequency generator 113 is configured to generate a radio-frequency pulse, for example, a radio-frequency excitation pulse. The radio-frequency excitation pulse is amplified (by, for example, a radio-frequency power amplifier (not shown)) and then applied to the RF transmit coil 112, so that the RF transmit coil 112 emits to the scan subject 16 an RF magnetic field B1 orthogonal to the static magnetic field B0 to excite nuclei in the body of the subject 16, and the longitudinal magnetization vector is converted into a transverse magnetization vector.

In one embodiment, the RF transmit coil 112 may be a body coil that may be connected to a transmit/receive (T/R) switch (not shown). The transmit/receive (T/R) switch is controlled so that the body coil can be switched between a transmit mode and a receive mode. In the receive mode, the body coil may be used for receiving the magnetic resonance signal from the subject 16. The RF transmit coil 112 may also be a local coil specifically used for a body part of the patient, such as a head coil.

After the end of the radio-frequency excitation pulse, a free induction decay signal, namely a magnetic resonance signal that can be acquired, is generated in the process that the transverse magnetization vector of the subject 16 is gradually restored to zero.

The gradient coil assembly 114 forms a gradient magnetic field in the imaging space so as to provide three-dimensional position information for the magnetic resonance signal described above. The magnetic resonance signal may be received by the RF receive coil 170 or a body coil in the receive mode.

The gradient coil assembly 114 may include three gradient coils. Each of the three gradient coils generates a gradient magnetic field inclined to one of three spatial axes (for example, X-axis, Y-axis, and Z-axis) perpendicular to each other, and generates a gradient field according to imaging conditions in each of a slice selection direction, a phase encoding direction, and a frequency encoding direction. More specifically, the gradient coil assembly 114 applies a gradient field in the slice selection direction of the subject 16 so as to select a slice; and the RF transmit coil 112 emits the RF excitation pulse to the slice selected by the scan subject 16 and excites the slice. The gradient coil assembly 114 also applies a gradient field in the phase encoding direction of the scan subject 16 so as to perform phase encoding on a magnetic resonance signal of the excited slice. The gradient coil assembly 114 then applies a gradient field in the frequency encoding direction of the subject 16 so as to perform frequency encoding on the magnetic resonance signal of the excited slice.

The gradient coil driver 115 is configured to respectively provide a suitable power signal for the aforementioned three gradient coils in response to a sequence control signal transmitted by the controller unit 130.

The RF receive coil 170 is configured to receive the aforementioned magnetic resonance signal with the three-dimensional position information. Depending on the imaging part, the RF receive coil 170 may include a surface coil array unit attached to the surface of the scan subject 16, and the RF receive coil 170 may further include a surface coil array unit disposed on a side of a table 120 back against the scan subject 16. The RF receive coil 170 should be positioned at a part of interest sufficiently close to the scan subject 16 so as to receive a magnetic resonance signal with high quality.

The data acquisition unit 117 is configured to acquire the magnetic resonance signal received by the RF receive coil 170. The data acquisition unit 117 may include, for example, a radio-frequency preamplifier, a phase detector, and an analog/digital converter, where the radio-frequency preamplifier is configured to amplify the magnetic resonance signal received by the RF receive coil 170 or the body coil, the phase detector is configured to perform phase detection on the amplified magnetic resonance signal, and the analog/digital converter is configured to convert the phase-detected magnetic resonance signal from an analog signal to a digital signal.

The data processing unit 140 may perform processing such as calculation and reconstruction on the digitized magnetic resonance signal so as to obtain a required image or image data. The data processing unit 140 may include a computer and a storage medium. A program of predetermined data processing to be executed by the computer is recorded on the storage medium. The data processing unit 140 may be connected to the data acquisition unit 117 to receive the magnetic resonance signal output by the data acquisition unit 117 so as to perform the aforementioned processing such as calculation and reconstruction. In one embodiment, the data processing unit 140 may include an image reconstruction unit 141 configured to reconstruct an image of an anatomical structure of the scan subject 16 based on the aforementioned image data.

The controller unit 130 is coupled to the scanner 110, the table 120, the data processing unit 140, and the operating console 150, so as to control corresponding components to perform required operations in a pre-scanning process or a scanning process for magnetic resonance imaging. For example, the controller unit 130 is configured to receive and process an operating signal input to the operating console 150, and control the working state of the aforementioned components such as the scanner 110 and the table 120 based on the operating signal. The operating signal may include, for example, protocols and parameters of scanning selected manually or automatically, the starting and stopping, lifting up and down, moving speed, and the like of the table 120, and communication information with the scan subject such as positioning guidance and warning. The controller unit 130 also controls the data processing unit 140 based on the operating signal received from the operating console 150 so as to obtain the desired image.

The controller unit 130 may include a computer and a storage medium, wherein the storage medium is configured to store a program executable by the computer, and when the computer executes the program, the components such as the scanner 110, the table 120, and the display unit 160 are enabled to perform corresponding operations in the pre-scanning process, the scanning process, or an apparatus maintenance process. The data processing unit 140 is also enabled to perform predetermined data processing.

In this embodiment, the controller unit 130 may control the starting and stopping, moving speed, and the like of the movable table board based on an operation instruction of a user or some detection signals, such that a part of interest of the scan subject 16 is positioned to be aligned with a scanning center of the magnetic resonance imaging system (for example, a center of the main magnet assembly) to facilitate imaging scanning on the part of interest. The controller unit 130 may further be configured to control other components of the scanner 110, the data processing unit 140, and the display unit 160.

Before the part of interest of the scan subject 16 is positioned, an auxiliary apparatus may be used to help rapidly position the scan subject at an appropriate part of the table 120, thereby avoiding excessive position adjustment of the scan subject for positioning the part of interest.

The auxiliary apparatus may be a positioning guidance device 180 coupled to the magnetic resonance imaging system, for example, a projection apparatus or an infrared apparatus for projecting a positioning mark onto the table 120, wherein the positioning mark is used for guiding the scan subject to be positioned relative to the table 120 in the pre-scanning process. The positioning guidance device 180 may be mounted on a housing of the main magnet assembly 111 or fixed above the table 120 in other mounting manners.

The storage media of the controller unit 130 and the data processing unit 140 may include, for example, a ROM, a floppy disk, a hard disk, an optical disk, a magneto-optical disk, a CD-ROM, or a non-volatile memory card.

The operating console 150 may include a user input apparatus, such as a keyboard and a mouse. An operator may input an operating signal/control signal to the controller unit 130 through the user input apparatus.

The display unit 160 may be connected to the operating console 150 to display an operation interface, and may further be connected to the data processing unit 140 to display reconstructed images or various images captured by a camera that is coupled to the magnetic resonance imaging system.

The MRI system 100 is described only as one example. In other embodiments, the MRI system 1 may have a plurality of transformations, as long as image data can be acquired from the imaging subject.

First Embodiment

Figure 2:
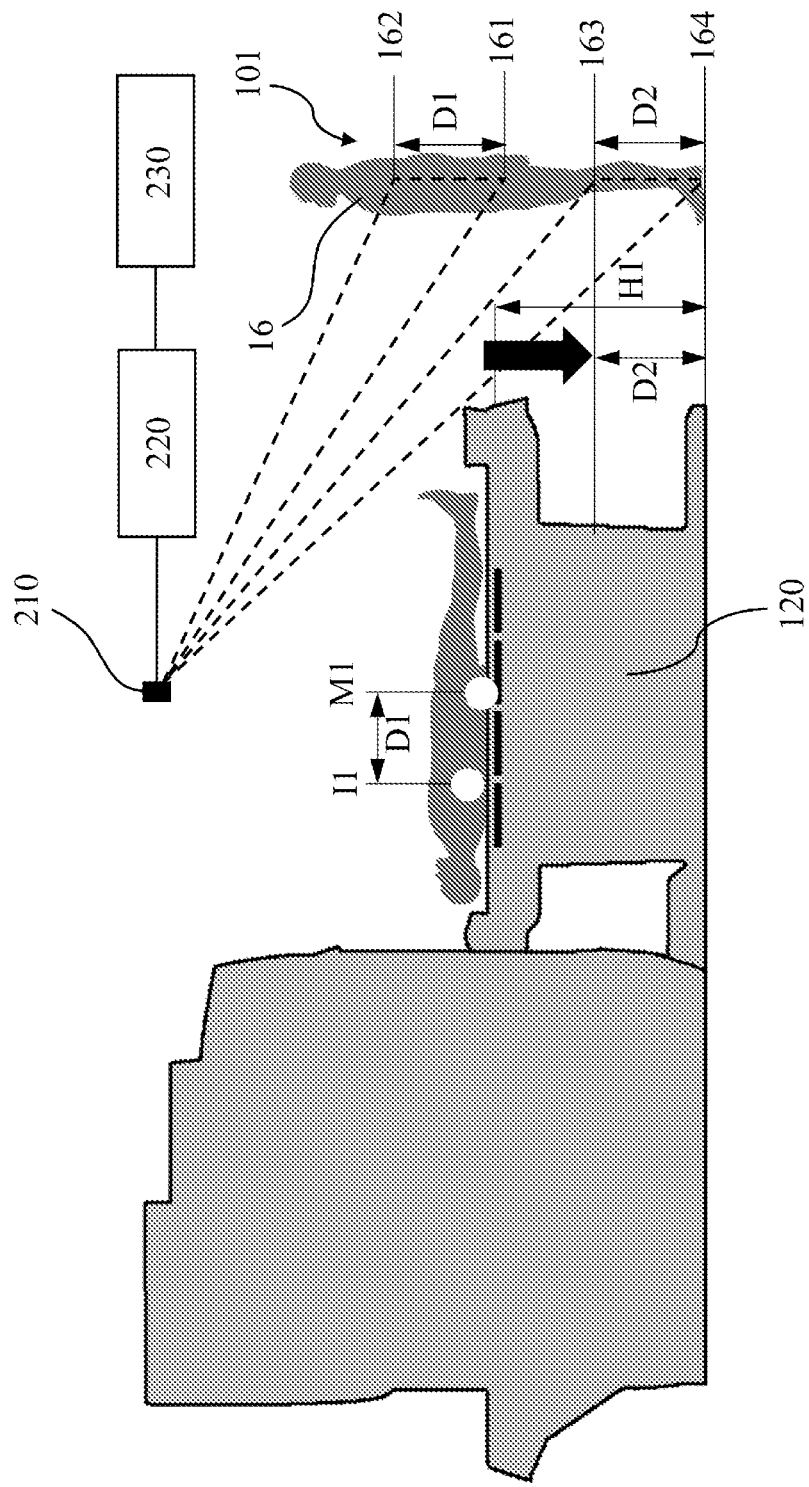
FIG. 2 shows a schematic structural diagram of a pre-scanning control system according to one embodiment of the present invention.

FIG. 2 shows a schematic structural diagram of a pre-scanning control system according to one embodiment of the present invention. The pre-scanning control system is used in a magnetic resonance imaging system. For example, the pre-scanning control system may be coupled to the magnetic resonance imaging system shown in FIG. 1. The pre-scanning control system may include a 3D camera 210, a processing device 220, and a control device 230.

The 3D camera is configured to obtain a three-dimensional image of the scan subject 16 located in the first region 101. As shown in FIG. 2, the 3D camera may be disposed at a higher position of the scanning room, for example, directly or obliquely above the table 120. The 3D camera may be fixed by using a ceiling of the scanning room or an apparatus at a higher position of the magnetic resonance imaging system.

As one example, when the scan subject starts to enter the scanning room, the scan subject 16 may be guided to pass through the first region 101 or stay briefly in the first region, so that the 3D camera can photograph the scan subject 16.

In one example, the first region 101 is opposite to a patient entrance of the scanning chamber 116 with respect to the table 120. That is, the table 120 is located between the first region 101 and the scanning chamber 116, and there is a space between the first region 101 and the table 120 to avoid interference when the scan subject 16 is photographed.

A captured first three-dimensional image at least includes a positioning part 161 and a part 162 of interest of the scan subject 16. The positioning part 161 is a feature part of a human body for ease of recognition in the image, for example, the hip.

The processing device 220 is configured (programmed) to determine first positioning information of the scan subject 16 based on a positional relationship between the positioning part 161 and the part 162 of interest of the three-dimensional image. The first positioning information is positioning information of the scan subject relative to the table 120 when the scan subject is subjected to an imaging scan. For example, the first positioning information may be used for indicating the position of the table 120 at which the positioning part 161 of the scan subject should be located, so that the part 162 of interest can exactly be opposite to a receive coil coupled within 120.

The part 162 of interest may be a part to be subjected to imaging diagnosis. The processing device 220 may determine a part of interest to be imaged according to a scanning protocol selected by a user through the operating console 150 and identify the part of interest in the three-dimensional image.

In one embodiment, the processing device 220 is configured to calculate a distance D1 between the positioning part 161 and the part 162 of interest in the three-dimensional image, and calculate the first positioning to information based on the distance D1 and second positioning information of the pre-identified part 162 of interest relative to the table 120.

The second positioning information is predetermined based on a position of the receive coil matching the part of interest relative to the table 120. In one embodiment, the receive coil is disposed in the movable table board of the table 120, and the second positioning information may be position information of the receive coil coupled in the table 120 relative to the table 120.

For example, assuming that the position where the receive coil coupled to the table 120 is denoted as I1, the position having a distance D1 from the point I1 is a positioning point of the positioning part 161 of the scan subject on the table 120.

The control device 230 is configured to control the positioning guidance device 180 to send positioning guidance information based on the aforementioned first positioning information. As described above with reference to FIG. 1, the positioning guidance device 180 may send positioning guidance information by projecting a guidance mark. For example, a guiding mark M1 is projected at the aforementioned positioning point of the table 120 to indicate that the positioning part (for example, the hip) of the scan subject 16 is located at the guiding mark. In this way, the scan subject can first sit at the guiding mark and then make the part of interest, such as the chest or another part, located exactly at an appropriate position (for example, at I1) when lying down.

Optionally, the three-dimensional image captured by the 3D camera 210 further includes at least two reference parts 163 and 164 of the scan subject 16. A height of lifting up and down of the table 120 may be controlled based on information of the reference parts 163 and 164, so that the scan subject 16 can more easily position the positioning part 161 thereof at the aforementioned appropriate position of the table 120. Specifically, the processing device 220 is configured to determine the height of the table 120 based on a positional relationship between the two reference parts 163 and 164 in the first three-dimensional image, and the control device 230 is configured to control 120 to be lifted up or down to the aforementioned height.

For example, the two reference parts 163 and 164 are respectively the knee part (for example, knee and knee pit) and foot (for example, sole, toes, and heel) of the scan subject, and the processing device 220 determines the height of the table 120 based on a distance D2 between the two reference parts 163 and 164. For example, the processing device 220 calculates a height D2 that is suitable for the current subject 16 to be scanned, while the current height of the table 120 is H1, then, the processing device 220 outputs H1-D2. When H1-D2 is greater than 0, the control device 230 controls the table 120 to be lifted down by H-D2; otherwise, the table 120 is controlled to be lifted up by D2-H.

The processing device 220 and the control device 40 may include a computer and a storage medium, where the storage medium is configured to store a program executable by the computer, and when the computer executes the program, the aforementioned positioning guidance of the scan subject can be implemented.

The processing device 220 and the control device 230 are preferably integrated with the computer and the storage medium of the magnetic resonance imaging system, and may also be configured independently.

Second Embodiment

The above embodiment describes positioning of a part of interest of a scan subject to a position corresponding to a receive coil disposed in the table 120. It should be understood that during magnetic resonance imaging, a surface coil that can cover a human body may further be used to receive magnetic resonance signals. It is usually desired that the surface coil is placed to be close enough to the part of interest (for example, the center of the part of interest opposite to the center of the surface coil), so that the received magnetic resonance signals have good enough quality.

Figure 3:
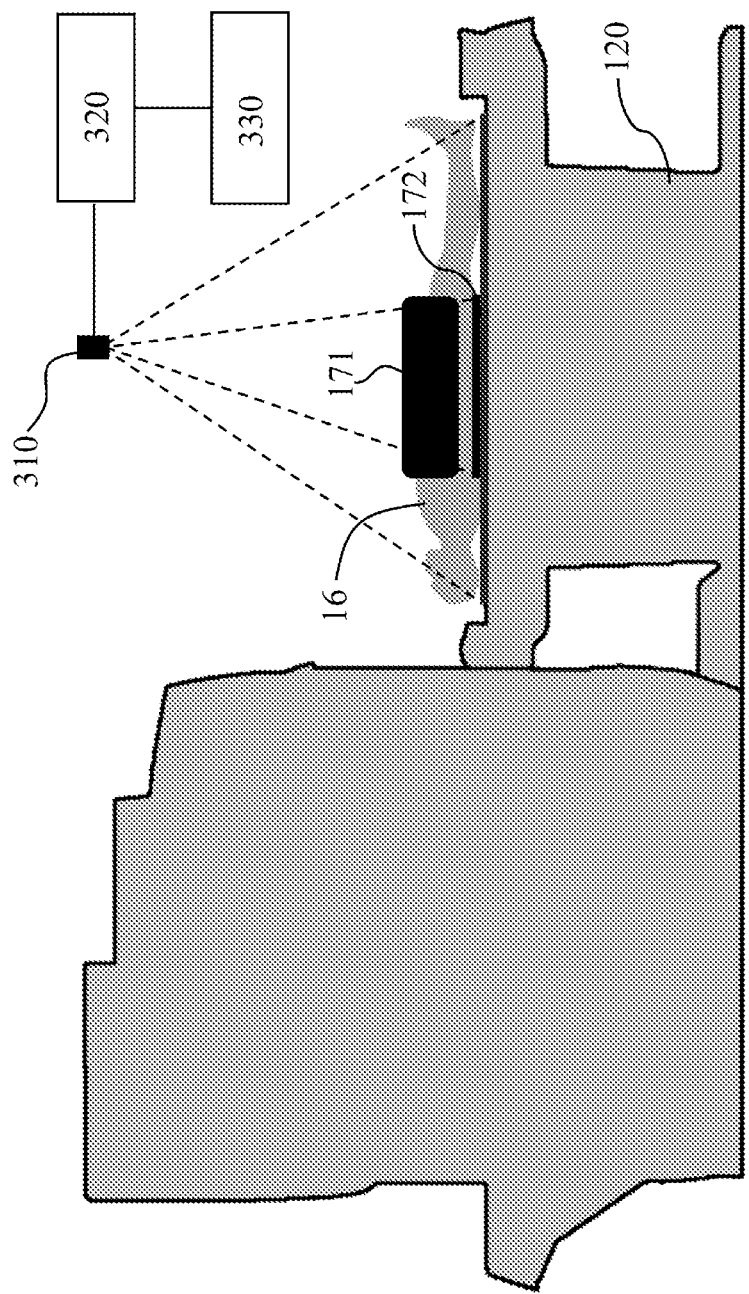
FIG. 3 shows a schematic structural diagram of a pre-scanning control system according to another embodiment of the present invention.

FIG. 3 shows a schematic structural diagram of a pre-scanning control system according to another embodiment of the present invention. As one example, the pre-scanning control system may be used in the magnetic resonance imaging system shown in FIG. 1. The pre-scanning control system provided in this embodiment can provide guidance/indication/warnings to a user so as to position the surface coil more rapidly. As shown in FIG. 3, the pre-scanning control system includes a 3D camera 310, a processing device 320, and a control device 330.

The 3D camera 310 may be the same apparatus as the 3D camera 210 or an apparatus mounted and disposed in a similar manner. The 3D camera 310 is configured to capture a three-dimensional image of a scan subject 16 located in the second region 102 and a surface receive coil 171 coupled to the scan subject. For example, when the scan subject 16 lies down or is positioned on the table 120 in other postures advantageous to scanning, and when the surface receive coil 171 is in position (for example, covers a part of interest of the human body), the 3D camera 310 may be used to obtain a three-dimensional image of the scan subject 16 and the surface receive coil 171 thereon.

The processing device 320 is configured (programmed) to determine, based on a positional relationship between the surface receive coil 171 and the scan subject 16 in the three-dimensional image, whether positions of the surface receive coil 171 and the part of interest of the scan subject match each other.

As one example, the processing device 320 may first respectively identify the surface receive coil 171 and the scan subject 16 in the three-dimensional image based on preset feature information of the surface receive coil 171 and the scan subject 16, wherein the feature information may include one or more of information such as the size, profile, and depth. The processing device 320 may determine the position of the part of interest in the identified scan subject based on predetermined distribution information of human anatomical structures, or may estimate the position of the part of interest through, for example, depth information, reflected in the three-dimensional image, wherein the position may be a range of position having a center position. The processing device 320 may further determine a center position of the identified surface receive coil, and determine whether the center position of the surface receive coil corresponds to the center position of the part of interest.

The control device 330 is configured (programmed) to control the magnetic resonance imaging system to issue a warning when positions of the surface receive coil 171 and the part of interest of the scan subject do not match. For example, the control device 330 may be coupled to the display unit 160 to control the display unit 160 to display mismatch information, wherein the mismatch information may further show a relative positional relationship of two center positions, for example, an offset and an offset direction, so as to inform the user how to adjust relative positions of the surface receive coil and the part of interest of the scan subject 16. The control device 330 may further be coupled to a voice apparatus of the magnetic resonance imaging system to inform the user of the aforementioned mismatch information.

Certainly, in this manner, it may be further determined whether the positions of the part of interest of the scan subject and the surface receive coil (for example, the surface receive coil 172 in FIG. 3) disposed in the table 120 match each other. For example, the processing device 320 may first identify the table 120 and the scan subject 16 in the image, and determine the position of the part of interest in the identified scan subject. Since the position of the surface receive coil 172 is fixed, that is, the surface receive coil has a predetermined positional relationship with respect to the table 120, therefore, the processing device 320 may further determine whether the position of the part of interest matches the position of the surface receive coil, and if not, the processing device may also issue mismatch information for the surface receive coil 172.

In one embodiment, when the same 3D camera is used to photograph the first region and the second region respectively, the control device 330 is further configured to control a photographing angle of the 3D camera so as to switch between a first photographing angle adapted to the first region 101 and a second photographing angle adapted to the second region 102.

Third Embodiment

Figure 4:
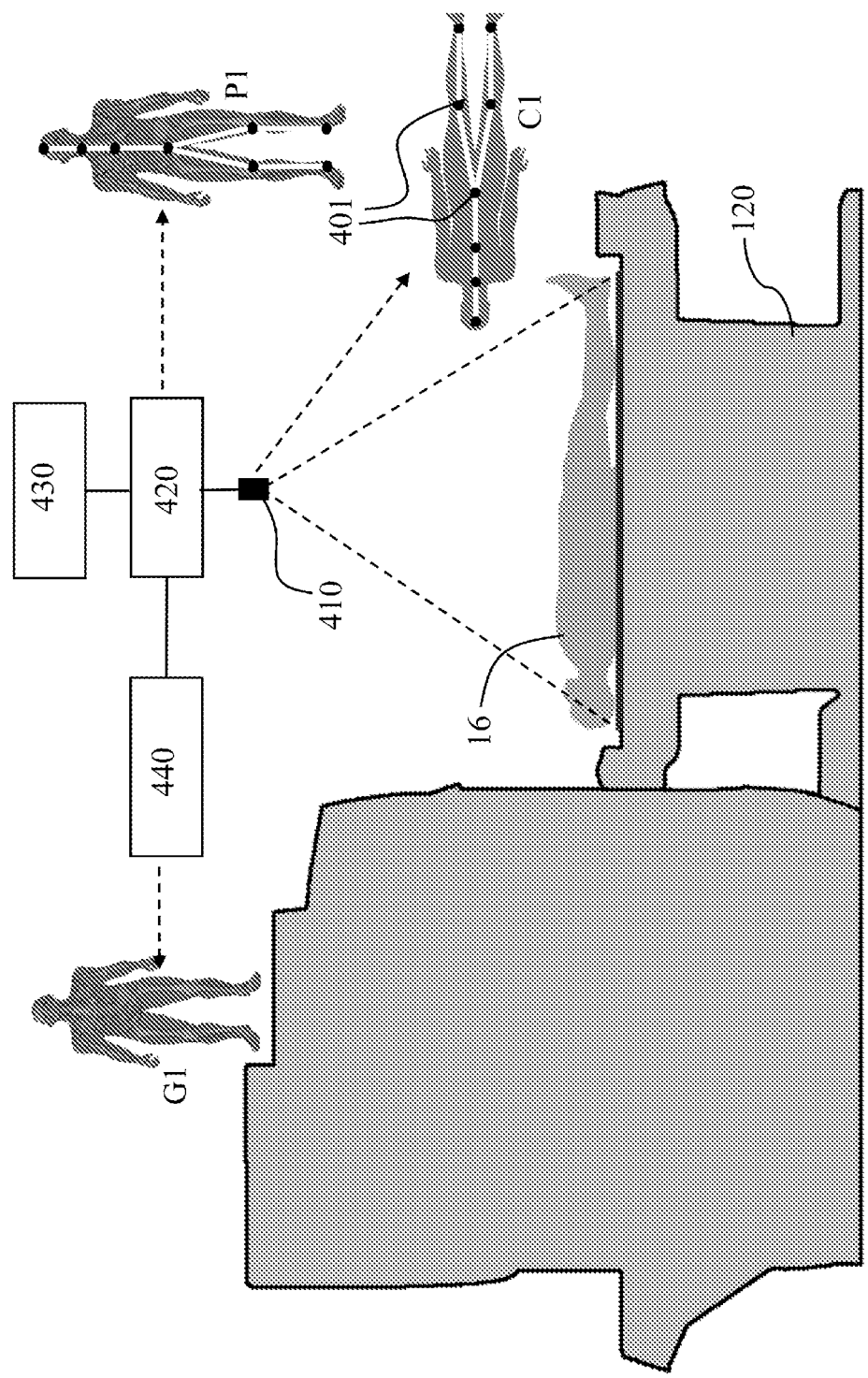
FIG. 4 shows a schematic structural diagram of a pre-scanning control system according to another embodiment of the present invention.

FIG. 4 is a schematic structural diagram of a pre-scanning control system according to another embodiment of the present invention. As one example, the pre-scanning control system may be used in the magnetic resonance imaging system shown in FIG. 1. As shown in FIG. 4, the pre-scanning control system includes a 3D camera 410, a processing device 420, a control device 430, and a storage device 440.

The storage device 440 is configured to store a standard human body image, such as the image G1 (Golden Image) shown in FIG. 4, wherein the standard human body image shows a plurality of human anatomical structures, such as various organs and bones. A plurality of different standard human body images may be stored based on the age group, gender, or other classification standards, so as to invoke an image matching a current scan subject in a pre-scanning process.

The 3D camera 410 may be the same apparatus as the 3D camera 310 or an apparatus mounted and disposed in a similar manner. The 3D camera 410 is configured to photograph the scan subject 16 located on the table 120. For example, when the scan subject 16 lies down or is positioned on the table 120 in other postures advantageous to scanning, the 3D camera 410 may be used to obtain a three-dimensional image C1 (Camera Image) of the scan subject 16.

The processing device 420 is configured to identify a plurality of feature points 401 from the aforementioned three-dimensional image C1, and determine a matching image P1 (Patient Image) of the standard human body image based on distribution information of the identified feature points 401, wherein the feature points of the three-dimensional image C1 can reflect body feature information of the scan subject 16, for example, one or more of the body proportion, body profile, body height, and body thickness. For example, parts in the standard human body image G1 (Golden Image) corresponding to the plurality of feature points may be adjusted to a similar distribution by processing such as scaling, local scaling, and proportion adjustment, so that a plurality of human anatomical structures in the standard human body image G1 are adapted to body features of the scan subject. In one example, the feature points 401 may include a plurality of points of main joints of the human body.

The aforementioned matching image P1 may be presented to the user through the display unit 160 of the magnetic resonance imaging system. A region of interest may be determined based on an operation on the matching image P1. For example, an operator may select an anatomical structure of interest (hereinafter referred to as a matching anatomical structure) in the matching image through auxiliary tools such as points, lines, or boxes. For example, the operator may select a matching anatomical structure 402 in the image P1 as a region of interest.

In other embodiments, the region of interest may be selected in other smarter manners, for example, image recognition and machine learning.

The processing device 420 is further configured to identify the region of interest selected from the matching image P1. The region of interest may be mapped to a body part of the scan subject 16. Generally, before a scanning program is executed, the center of the region of interest of the scan subject 16 needs to be aligned with the scanning center, which needs to be implemented through movement of the table 120.

The control device 430 is coupled to the table 120 of the magnetic resonance imaging system. Based on the region of interest identified by the processing device 420, the control device 430 is configured to control movement of the table 120, so as to position the body part of the scan subject 16 corresponding to the region of interest to a preset position.

The aforementioned preset position may be an imaging position determined in the imaging region, for example, a position in the scanning chamber 116 opposite to the scanning center.

Fourth Embodiment

For example, in the magnetic resonance imaging system shown in FIG. 1, a main magnetic field provided by the main magnet assembly 111 is not uniform, and varies throughout the imaging region. The imaging region may be considered as having a spatial field gradient (for example, variation in field intensity in the Z direction), wherein the spatial field gradient may be different in different ranges of position in the imaging region.

Figure 5:
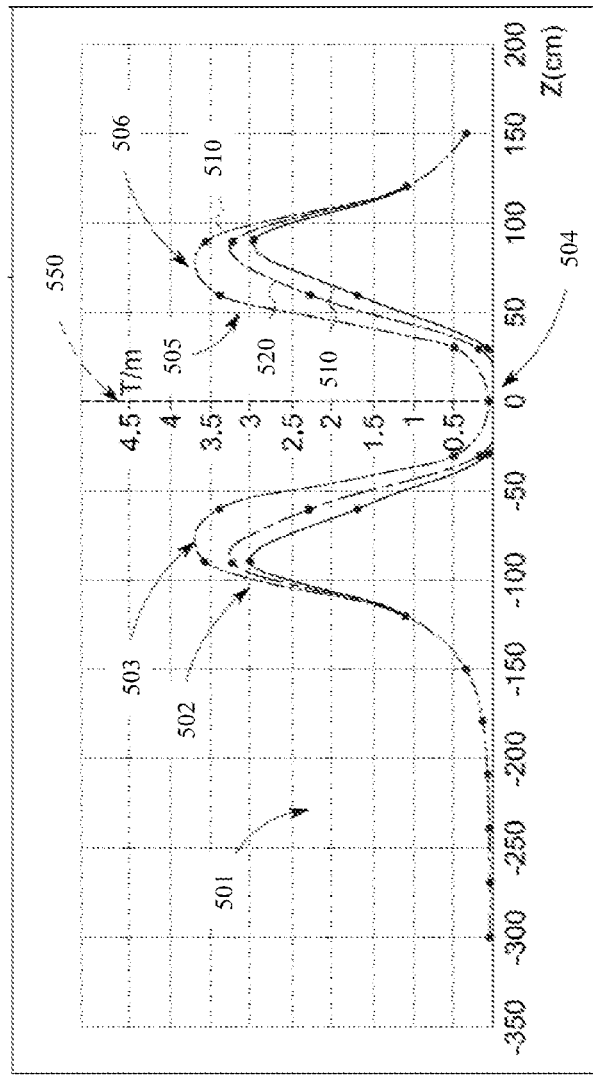
FIG. 5 is an exemplary diagram of a spatial field gradient that varies with position in a moving direction of a movable table board.

FIG. 5 is an exemplary diagram of a spatial field gradient that varies with position in a moving direction (namely, the Z direction) of the movable table board. The horizontal axis in FIG. 5 represents a linear position along the Z direction, and the vertical axis represents a spatial field gradient, wherein a positive displacement value and a negative displacement value with respect to a scanning center 550 are used to mark the linear position of the horizontal axis. In one embodiment, the spatial field gradient is in units of Tesla/meter (T/m). According to FIG. 5, the human body is subjected to a varying field at different positions in the Z direction.

In addition, the amplitude of the spatial field gradient varies with the body size of the patient. As an example, FIG. 5 shows three spatial field gradient curves 510, 520, and 530 for patients with large, medium, and small size bodies respectively.

As shown in FIG. 5, each of the curves 510, 520, and 530 has a substantially similar shape. For example, at an entrance portion 501 from −300 centimeters to −200 centimeters, the gradient is zero or near zero. The entrance portion 501 corresponds to a range of position in which the brain of the human body is completely or almost completely outside a cavity 112 and a defined imaging region thereof.

Then, a first portion 502 of each gradient curve beginning at about −200 centimeters corresponds to a portion in which the brain enters the imaging region and becomes close to the scanning center 550. At about −80 centimeters of the example shown, the gradient reaches a peak value 503, and then the gradient decreases as the curve is closer to the scanning center 550.

A second portion 504 of each gradient curve is on the other side of the scanning center 550 and at a distance of about 20 centimeters from the scanning center 450, and corresponds to a position where the brain of the human body is at the scanning center 550 or near the scanning center 550. For the second portion 504, the gradient is zero or relatively low.

If the brain of the human body further move forward and gradually away from the scanning center 550, it would meet a third portion 505 of each curve. At about 80 centimeters of the example shown, the gradient reaches a peak value 506, and then the gradient decreases as the brain gradually approaches a farther edge of the field in the imaging region.

It is generally believed that the brain of the human body is more affected by field variations than other parts of the human body. Moreover, the patient comfort is usually related to field variations with time, rather than field variations with distance. As a result, the traveling speed of the brain passing through different spatial gradient fields needs to be controlled to avoid discomfort or accidents.

Figure 6:
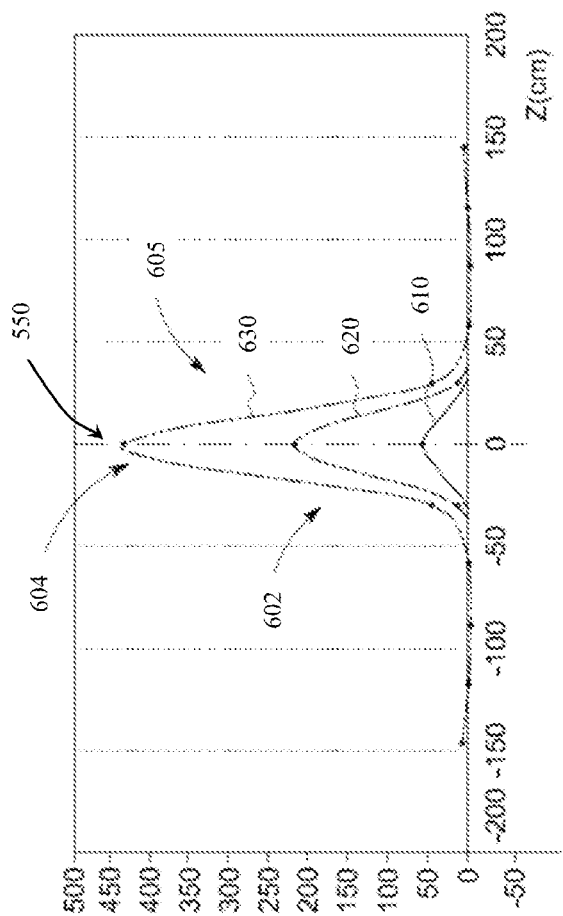
FIG. 6 is an exemplary diagram of a moving speed of the movable table board that varies with the position in the moving direction thereof.

Accordingly, FIG. 6 is an exemplary diagram of a moving speed of the movable table board that varies with the position in the moving direction (Z direction) thereof. The horizontal axis in FIG. 6 represents a linear position in the Z direction, which is specifically represented by a positive displacement value and a negative displacement value with respect to the scanning center 550. The vertical axis in FIG. 6 represents the maximum speed limit, namely, the safety speed, of the movable table board at the corresponding position. FIG. 6 shows three moving speed curves 610, 620, and 630 for patients with large, medium, and small size bodies respectively. According to FIG. 6, since the spatial field gradient is high for a patient with a large size, the speed curve 610 includes speeds lower than other curves. Typically, each curve represents a low speed in the case of a high gradient and a high speed in the case of a low gradient. Each of the curves 610, 620, and 630 includes: a first position 602, corresponding to the first portion 502 of the curve in FIG. 5; a second portion 604, corresponding to the second portion 504; and a third portion 605, corresponding to the third portion 505.

Figure 7:
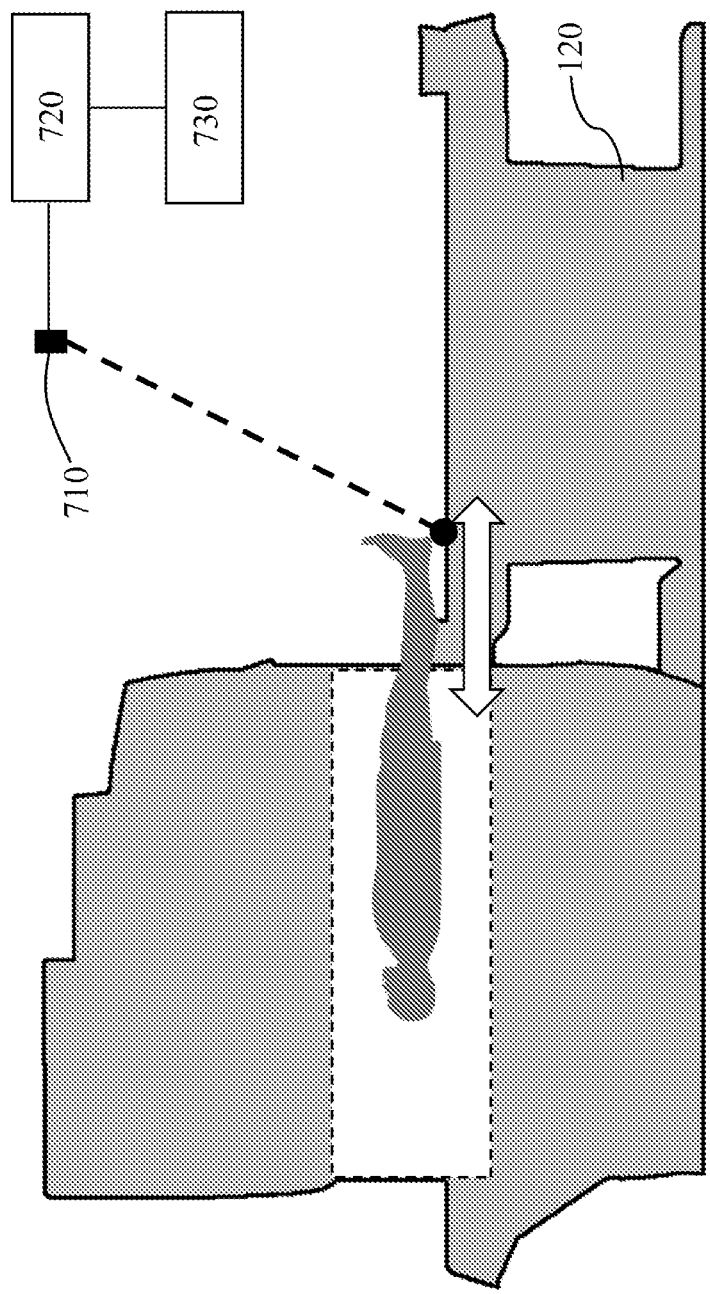
FIG. 7 shows a schematic structural diagram of a pre-scanning control system according to another embodiment of the present invention.

FIG. 7 shows a schematic structural diagram of a pre-scanning control system according to another embodiment of the present invention. The pre-scanning control system is used in a magnetic resonance imaging system. For example, the pre-scanning control system may be coupled to the magnetic resonance imaging system shown in FIG. 1. As shown in FIG. 7, the pre-scanning control system includes a 3D camera 710, a processing device 720, and a control device 730.

The 3D camera 710 may be the same apparatus as the 3D cameras 210, 310, 410 or an apparatus mounted and disposed in a similar manner. The 3D camera 710 is configured to photograph the scan subject 16 on the table 120. For example, when the scan subject 16 lies down or is positioned on the table 120 in other postures advantageous to scanning, the 3D camera 710 may be used to obtain a three-dimensional image of the scan subject 16.

On one hand, the processing device 720 is configured (programmed) to obtain a curve of the moving speed of the table 120 varying with the position in the Z direction, wherein the curve may be, for example, the curve shown in FIG. 6. The processing device 710 may, for example, obtain a spatial field gradient curve shown in FIG. 5 in advance, and then obtain a speed curve of the table 120 shown in FIG. 6 based on the spatial field gradient curve. Speed curves corresponding to different body sizes may be prestored in the storage device coupled to the processing device 720, and the processing device 720 invokes a corresponding speed curve based on a body size of the scan subject that is inputted in advance.

On the other hand, the processing device 720 is configured to identify the head of the scan subject 16 in the three-dimensional image captured by the aforementioned 3D camera, calculate a current position of the head of the scan subject 16 based on an identification result, and predict a moving speed of the scan subject 16 based on the current position of the head of the scan subject.

The control device 730 is configured to be coupled to a driver of the table 120 and control the table 120 based on the predicted moving speed of the scan subject 16. For example, the scan subject may be moved more rapidly through portions (for example, the entrance portion 501 and the second portion 504) in which the spatial field gradient is relatively low, and moved more slowly through portions (for example, the first portion 502 and the third portion 505) in which the spatial field gradient is relatively high.

Upon completion of the scan, the moving speed of the table 120 can be controlled in a similar manner according to the aforementioned spatial field gradient, so as to move the scan subject 16 out of the scanning chamber.

Based on the above embodiment, the present invention may further provide a pre-scanning control method fora magnetic resonance imaging system. FIG. 8, FIG. 9, FIG. 10, and FIG. 12 respectively show flowcharts of one embodiment of the pre-scanning control method. FIG. 11 shows a flowchart of one embodiment of controlling movement of a scanning table in FIG. 10.

Figure 8:
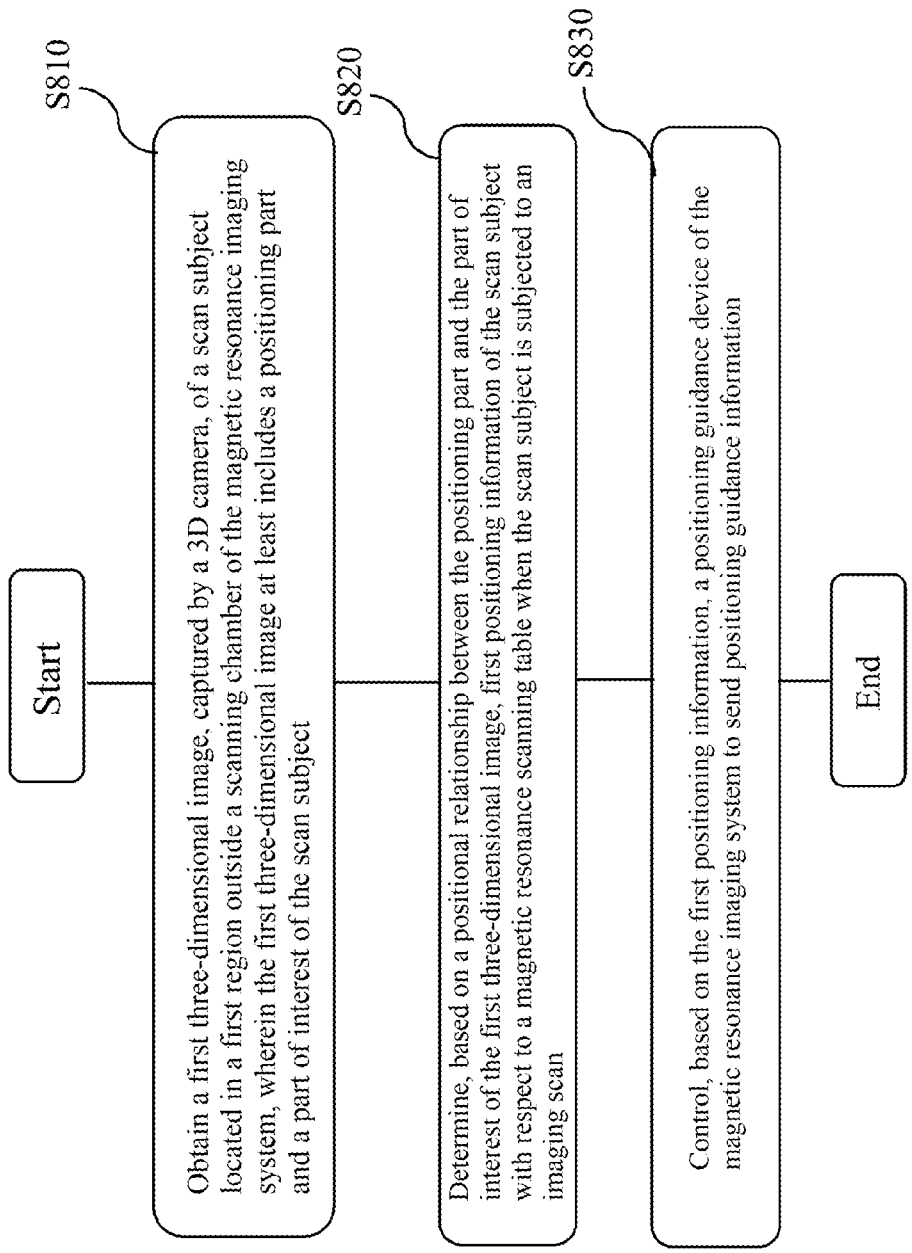
FIG. 8, FIG. 9, FIG. 10, and FIG. 12 respectively show flowcharts of one embodiment of a pre-scanning control method.
Figure 9:
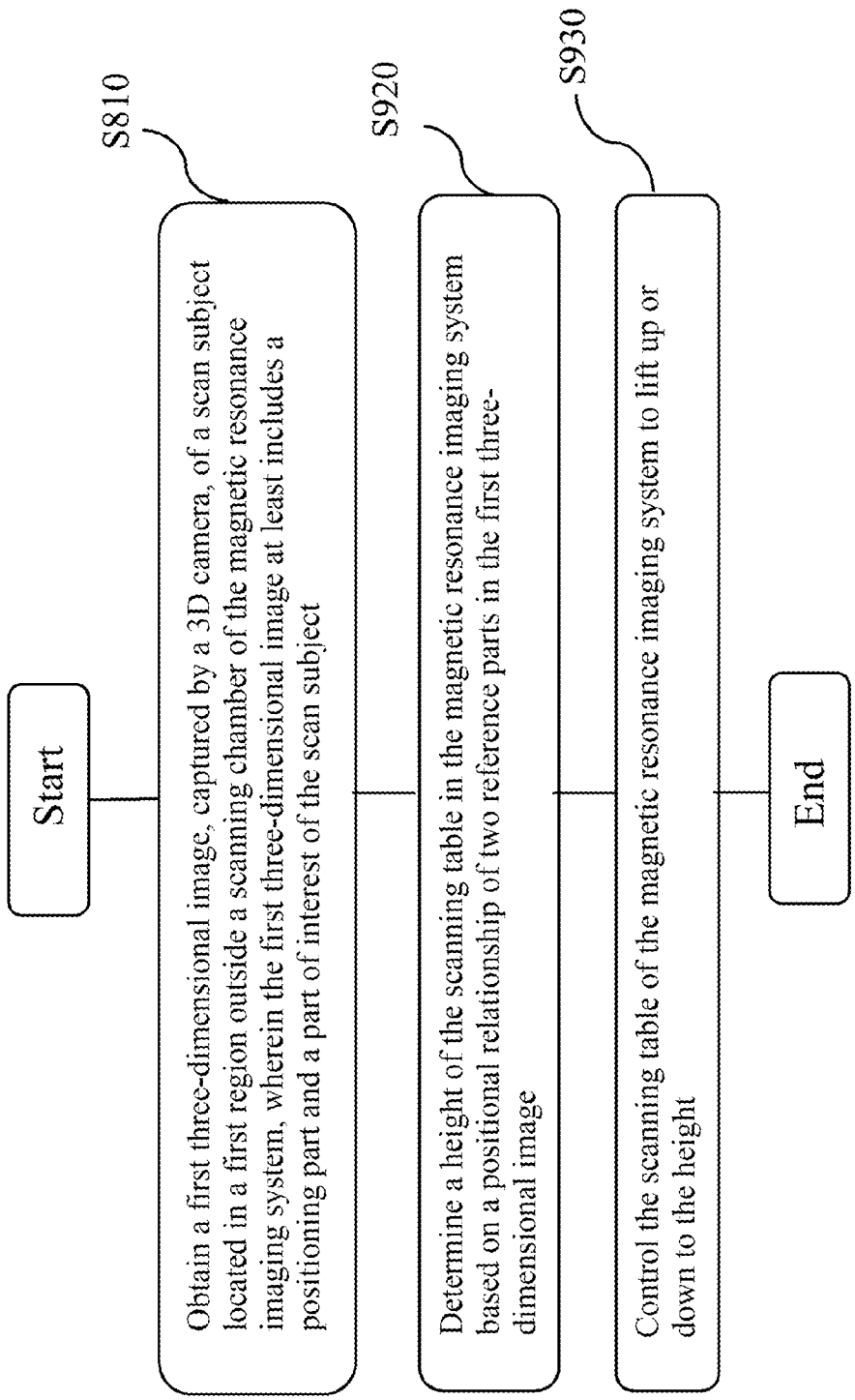

As shown in FIG. 8, in one embodiment, the pre-scanning control method includes steps S810 to S830.

In step S810, a first three-dimensional image, captured by a 3D camera, of a scan subject located in a first region outside a scanning chamber of the magnetic resonance imaging system is obtained, wherein the first three-dimensional image at least includes a positioning part (for example, the hip) and a part of interest (for example, the chest) of the scan subject.

In step S820, when the scan subject is subjected to an imaging scan, first positioning information of the scan subject with respect to a magnetic resonance scanning table (for example, the table 120) is determined based on a positional relationship between the positioning part and the part of interest of the first three-dimensional image.

In step S830, a positioning guidance device (for example, the device 180 shown in FIG. 1) of the magnetic resonance imaging system is controlled to send positioning guidance information based on the first positioning information.

Step S820 may further include: calculating a distance between the positioning part and the part of interest in the first three-dimensional image, and calculating the first positioning information based on the distance between the positioning part and the part of interest and predetermined second positioning information of the part of interest with respect to the magnetic resonance scanning table.

Further, the second positioning information is determined based on a position of a receive coil (for example, the receive coil 171) matching the part of interest with respect to the magnetic resonance scanning table, and the receive coil is disposed on the magnetic resonance scanning table.

The aforementioned first three-dimensional image at least includes two reference parts of the scan subject, for example, the knee and foot. The method shown in FIG. 9 includes steps S910 and S920.

In step S910, a height of the scanning table in the magnetic resonance imaging system is determined based on a positional relationship between two reference parts in the first three-dimensional image. In step S920, the scanning table is controlled to be lifted up or down to the height.

In step S910, the height of the scanning table may be determined based on a distance between the two reference parts in the first three-dimensional image.

Figure 10:
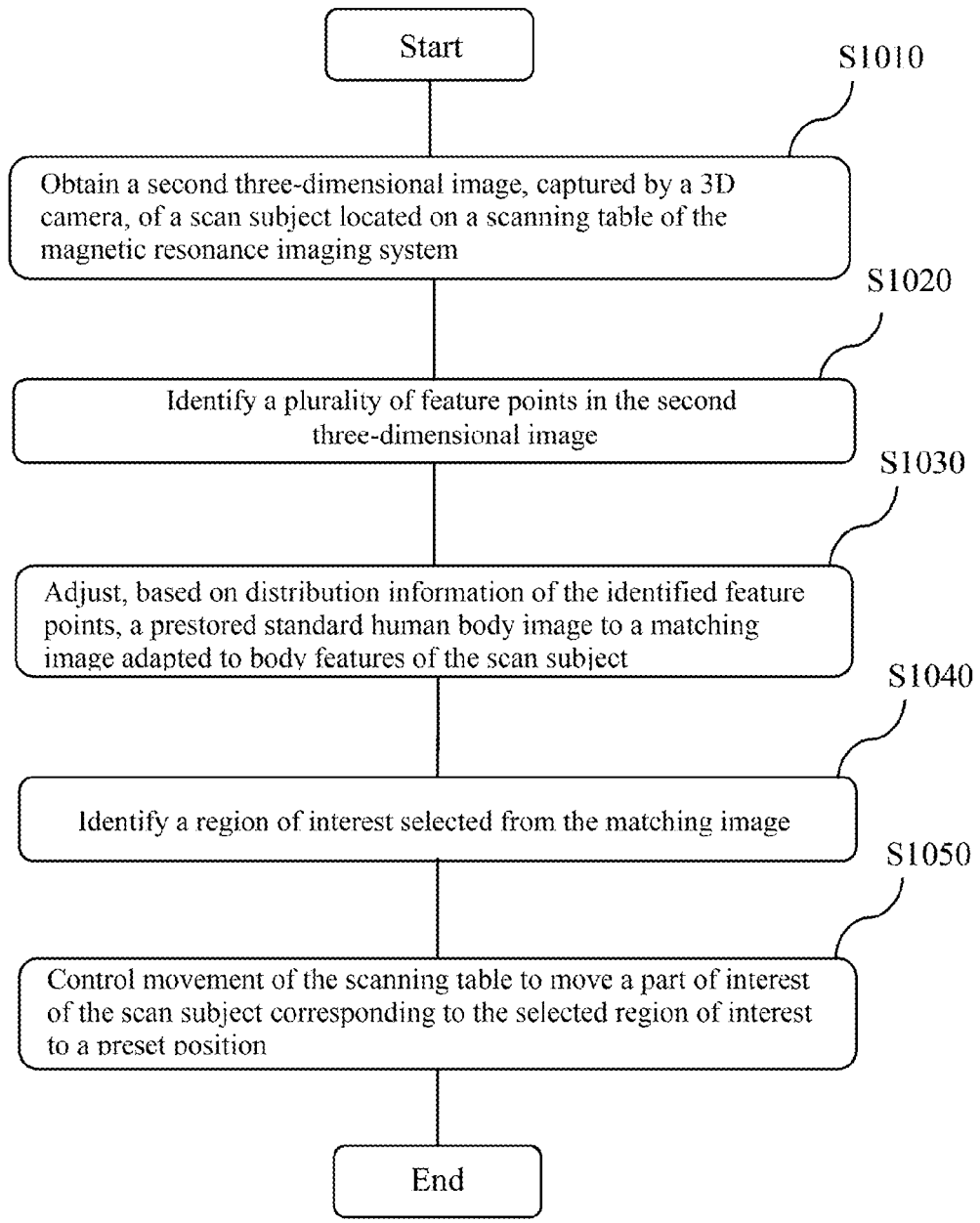
Figure 11:
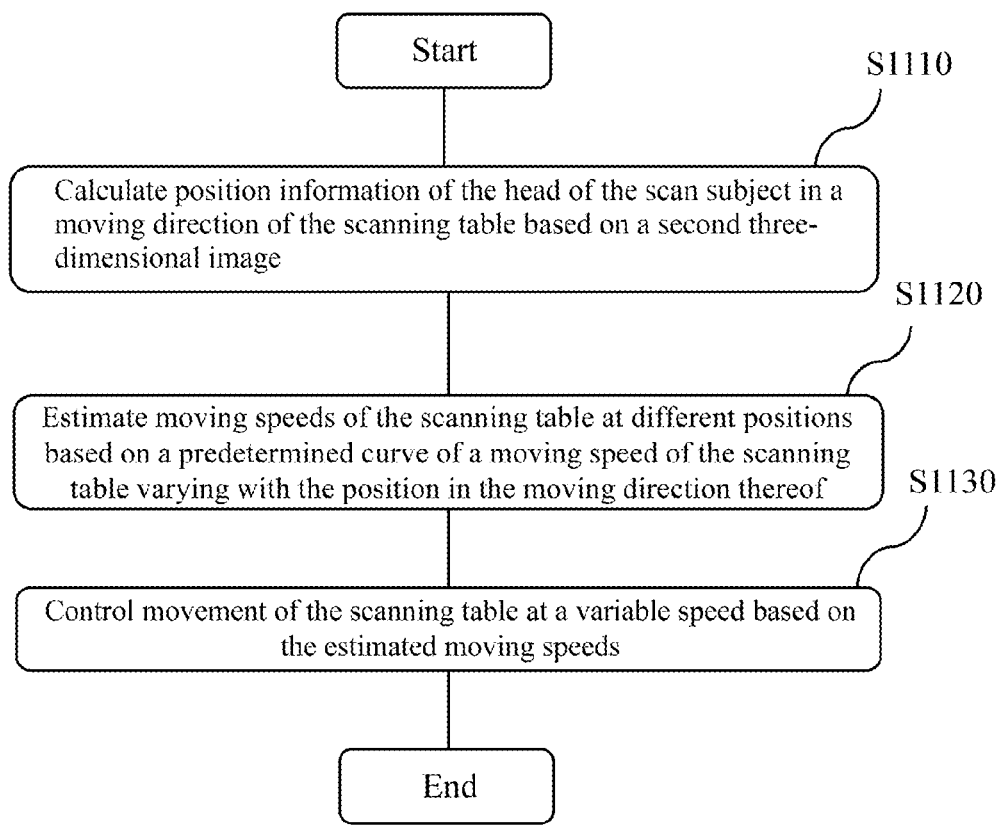
FIG. 11 shows a flowchart of one embodiment of controlling movement of a scanning table in FIG. 10.

The scanning control method shown in FIG. 10 includes steps S1010 to S1050.

In step S1010, a second three-dimensional image, captured by a 3D camera, of a scan subject located on a scanning table (for example, the table 120) of the magnetic resonance imaging system is obtained.

In step S1020, a plurality of feature points (for example, the feature points 401 in FIG. 4) is identified in the second three-dimensional image.

In step S1030, a prestored standard human body image (for example, the image G1 in FIG. 4) is adjusted to a matching image (for example, the image P1 in FIG. 4) adapted to body features of the scan subject based on distribution information of the identified feature points.

In step S1040, a region of interest (for example, the region 402 in FIG. 4) selected from the matching image is identified.

In step S1050, movement of the scanning table is controlled to position a part of interest of the scan subject corresponding to the selected region of interest (for example, the chest of the patient corresponding to the region 402 of interest) to a preset position.

The controlling movement of the scanning table may further include controlling movement of the scanning table at a variable speed. FIG. 11 shows a flowchart of one embodiment of controlling movement of a scanning table. As shown in FIG. 11, the flow specifically includes steps S1110 to S1130.

In step S1110, position information of the head of the scan subject in a moving direction of the scanning table is calculated based on a second three-dimensional image. The position information of the head of the scan subject in the moving direction of the scanning table includes a distance between the head of the scan subject and a scanning center of a magnetic resonance imaging system.

In step S1120, moving speeds of the scanning table at different positions is estimated based on a predetermined curve of a moving speed of the scanning table varying with the position in the moving direction thereof.

In step S1130, movement of the scanning table at a variable speed is controlled based on the estimated moving speeds.

Figure 12:
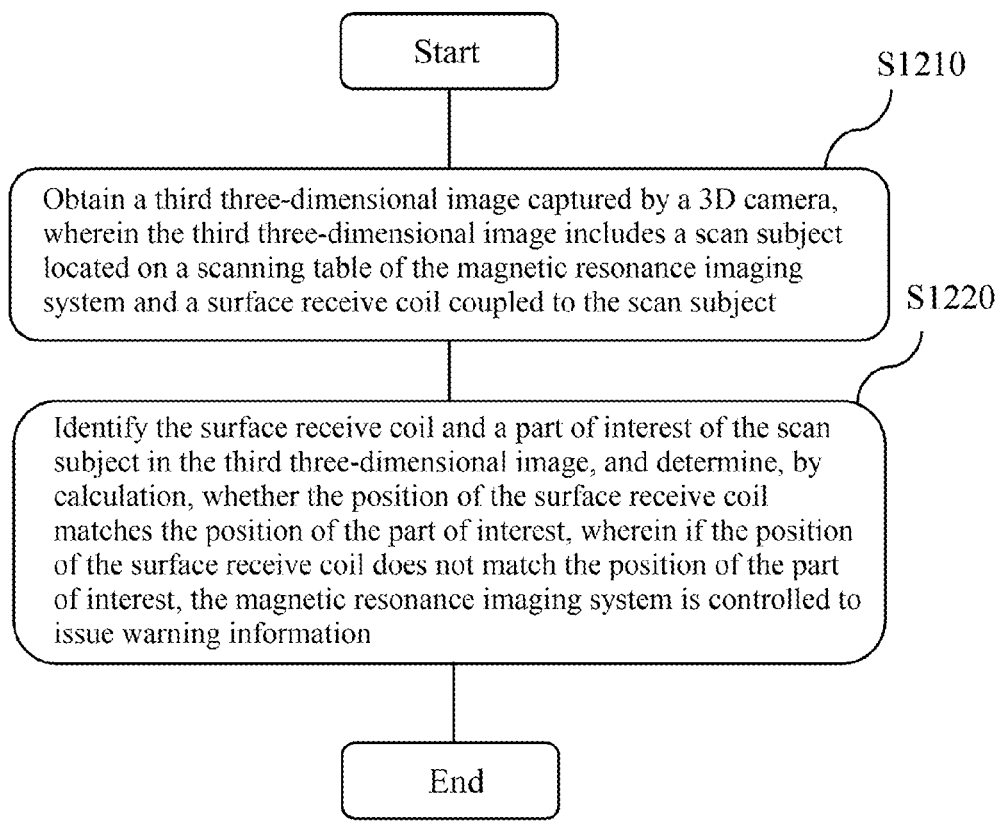

As shown in FIG. 12, in one embodiment, the pre-scanning control method includes steps S1210 to S1220.

In step S1210, a third three-dimensional image captured by a 3D camera (for example, the 3D camera 310) is obtained, wherein the third three-dimensional image includes a scan subject located on a scanning table of the magnetic resonance imaging system and a surface receive coil coupled to the scan subject.

In step S1220, the surface receive coil and a part of interest of the scan subject is identified in the third three-dimensional image, and it is determined by calculation whether the position of the surface receive coil matches the position of the part of interest, wherein when the position of the surface receive coil does not match the position of the part of interest, the magnetic resonance imaging system is controlled to issue warning information.

Fifth Embodiment

Figure 13:
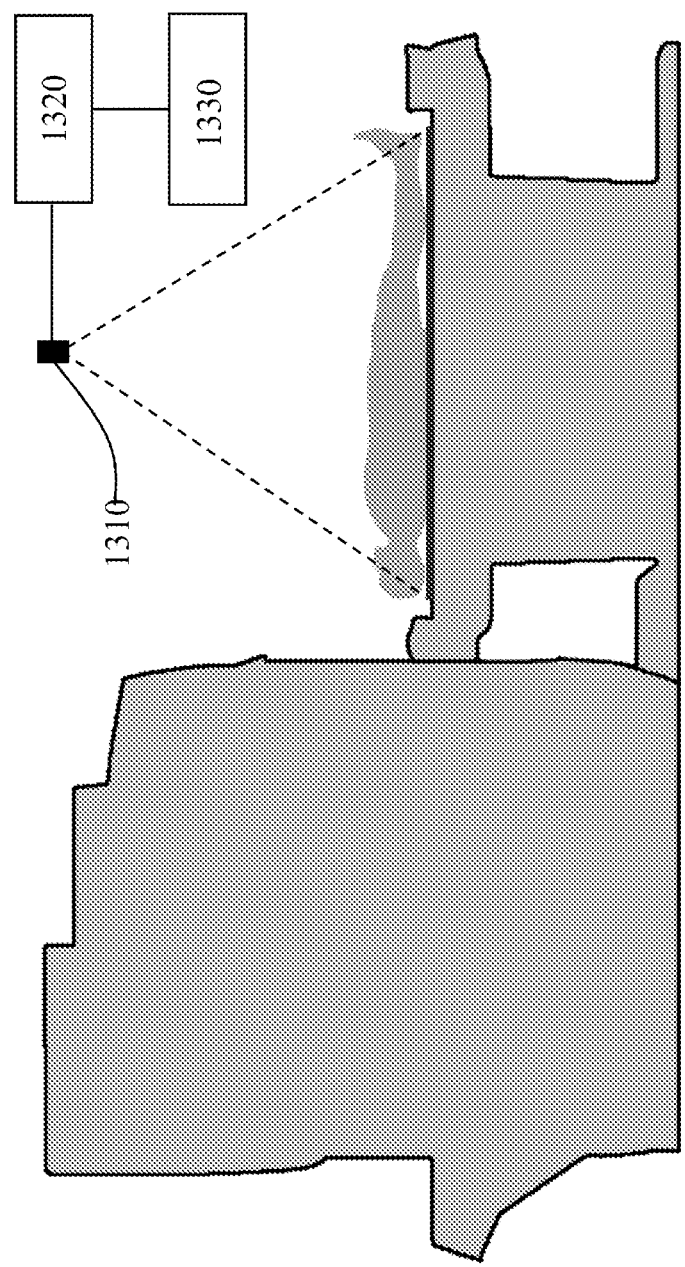
FIG. 13 shows a schematic structural diagram of a scanning control system according to one embodiment of the present invention.

FIG. 13 shows a schematic structural diagram of a scanning control system according to an embodiment of the present invention. The scanning control system is used in a magnetic resonance imaging system. For example, the scanning control system may be coupled to the magnetic resonance imaging system shown in FIG. 1. The scanning control system may include a 3D camera 1310, a processing device 1320, and a control device 1330.

The 3D camera 1310 may be the same apparatus as the 3D cameras 210, 310, 410, 710 or an apparatus mounted and disposed in a similar manner. The 3D camera 1310 may be configured to photograph the scan subject 16 located on the table 120. For example, when the scan subject 16 lies down or is positioned on the table 120 in other postures advantageous to scanning, the 3D camera 1310 may be used to obtain a three-dimensional image of the scan subject 16. In one embodiment, when the 3D camera 1310 is the same apparatus as the 3D camera 210, the photographing angle of the camera may be switched based on identification of different stages of magnetic resonance imaging. For example, when the current stage is identified as patient positioning, the 3D camera may be focused on the aforementioned scan subject in the first region; when the current stage is identified as a scanning stage, the 3D camera 1310 may be focused on the scan subject 16 on the table 120. The photographing angle of the 3D camera may be switched by, for example, the control device 1330.

Figure 14:
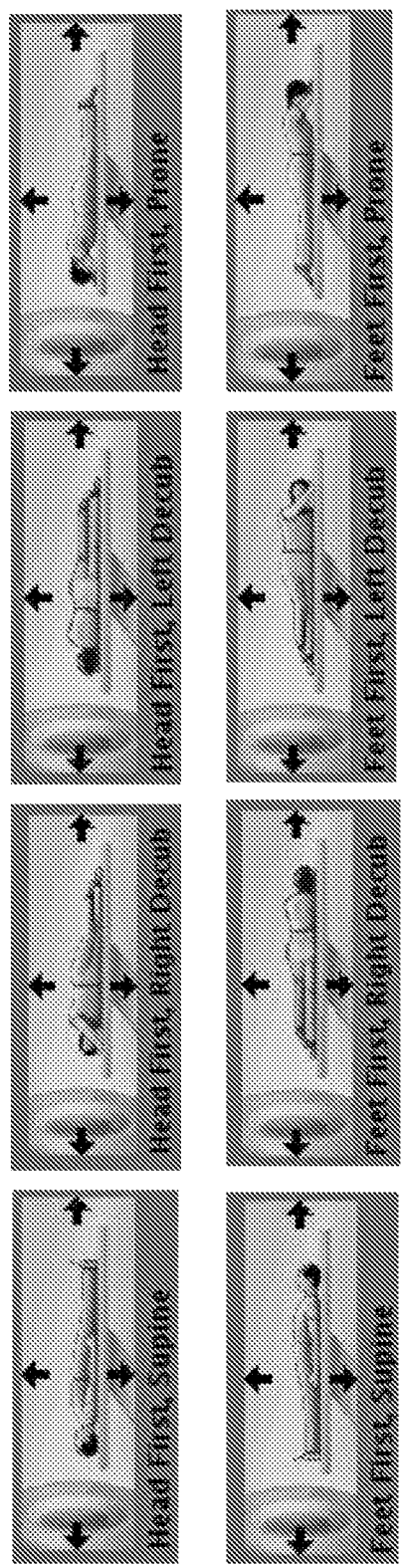
FIG. 14 shows an exemplary diagram of a scan subject in a plurality of body positions.

The processing device 1320 is configured to identify body position information of the scan subject 16 based on the three-dimensional image captured by the 3D camera 1310, wherein the body position information is used for representing a positioning direction and posture of the scan subject 16 on the table 120. FIG. 14 exemplarily shows a plurality of body positions of the scan subject.

The positioning direction may usually include, for example, head first or feet first, namely, the head enters the scanning chamber first or the feet enter the scanning chamber first when the table 120 is moved to make the scan subject thereon enter the scanning chamber from the outside. For example, the 4 body positions in the upper part of FIG. 14 are head first, and the 4 body positions in the lower part are feet first. The positioning posture may include, for example, supine position, left lateral decubitus position, right lateral decubitus position, and prone position.

Typically, in a scanning stage of magnetic resonance imaging, a doctor or technician needs to input corresponding body position information based on a positioning direction and posture of a patient so as to subsequently select an appropriate slice position for image reconstruction. Sometimes, the body position information input by the doctor or technician is inconsistent with the actual situation, so that an image reconstructed by the magnetic resonance imaging system does not correspond to a lesion part of the patient. In this case, the patient often needs to be re-scanned, causing waste of medical resources and emotional problems of the patient.

In this embodiment, the processing device 1320 may automatically identify the aforementioned body position information of the scan subject 16 based on the three-dimensional image captured by the 3D camera 1310, so that the control device 1330 can set scanning parameters related to a body position based on the identified body position information, wherein the scanning parameters may include body position information, or may also include other parameters that change due to the change in the body position. In this way, the aforementioned problems caused by manual input of body position information are avoided, and the scanning setting time can be reduced. In one embodiment, the image reconstruction unit 141 may determine a slice position and angle for image reconstruction based on the set parameters related to the body position, so as to obtain an image that facilitates disease diagnosis.

The body position information inputted in the conventional manner is usually general information. Taking lateral decubitus position for example, a plurality of different postures of a patient may be included, and thus it is difficult for a slice position and angle selected in the subsequent reconstruction process to more precisely correspond to a lesion part.

Therefore, the processing device 1320 may further more precisely determine, based on the body position of the scan subject 16 displayed in the three-dimensional image, a slice position and angle for image reconstruction, and send the determined slice position and angle to an image reconstruction unit (for example, the image reconstruction unit 141 in FIG. 1) of the magnetic resonance imaging system. The slice position and angle are determined based on the real body position of the scan subject 16 displayed in the three-dimensional image. For example, the selected slice may not be limited to be in an X-Y plane, and may further form an angle with the X-Y plane, so that an image reconstructed by the image reconstruction unit can more precisely correspond to a lesion part or part of interest of the scan subject.

Sixth Embodiment

Figure 15:
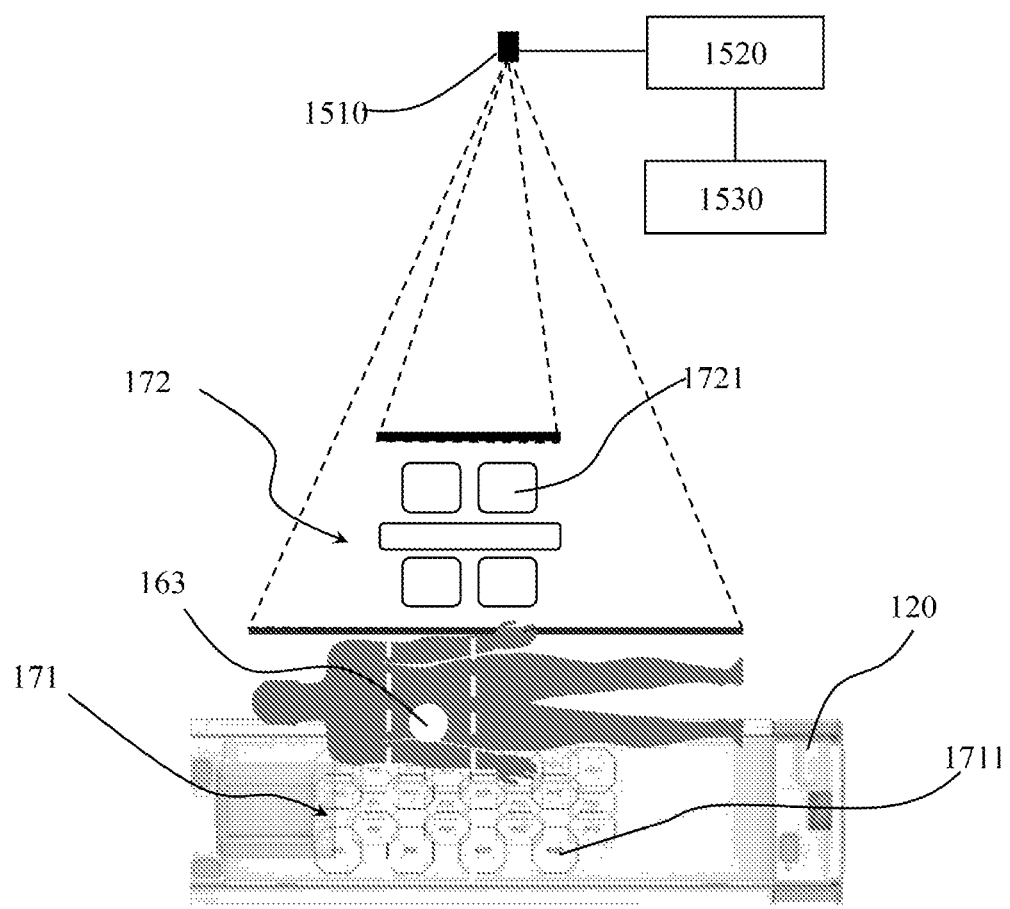
FIG. 15 shows a schematic structural diagram of a scanning control system according to another embodiment of the present invention.

FIG. 15 shows a schematic structural diagram of a scanning control system according to another embodiment of the present invention. The scanning control system is used in a magnetic resonance imaging system. For example, the scanning control system may be coupled to the magnetic resonance imaging system shown in FIG. 1. The scanning control system may include a 3D camera 1510, a processing device 1520, and a control device 1530.

The 3D camera 1510 may be the same apparatus as the 3D cameras 210, 310, 410, 710, 1310 or an apparatus mounted and disposed in a similar manner.

The 3D camera 1510 is configured to photograph the table 120 and the scan subject 16 located on the table 120 to obtain a three-dimensional image. The scan subject 16 is coupled to an RF receive coil, the RF receive coil may include a first receive coil 171 disposed in the table 120, and the first receive coil 171 includes a plurality of coil units 1711 arranged in an array. Referring to FIG. 1 and FIG. 15 in combination, the first receive coil 171 may be disposed on a side of the table 120 facing away the scan subject 16, a positional relationship between the first receive coil and the table 120 is determined, and the positional relationship may be represented by second relative position information. Specifically, the second relative position information may include a range of position or a central position of the coil unit 1711 on the table 120.

When the first receive coil 171 is selected to be turned on, the processing device 1520 selects an appropriate coil unit 1711 in the first receive coil 171 to obtain image data of the scan subject. For example, the processing device 1520 may determine first relative position information of a part of interest of the scan subject 16 and the table 120 based on the three-dimensional image captured by the 3D camera 1510, wherein the first relative position information may specifically represent a range of position or a central position of a region 163 of interest of the scan subject 16 on the table 120. The processing device 1520 may identify the table and the region 163 of interest of the scan subject in the three-dimensional image, and calculate a positional relationship between the region 163 of interest and the table 120 that are identified as the first relative position information.

The processing device 1520 further determines relative position information of a part 162 of interest of the scan subject 16 and the first receive coil 171 based on the first relative position information and the second relative position information, and determine a coil unit 1711 required to be turned on in the first receive coil 171 based on the relative position information of the part 162 of interest of the scan subject 16 and the first receive coil 171. For example, the processing device 1520 determines a coil unit 1711 closer to the region 163 of interest of the scan subject 16.

The control device 1530 is configured to turn on the determined coil unit 1711. Specifically, the control device 1530 turns on the coil unit 1711 by controlling a switch of the coil unit 1711.

An example of automatically selecting a coil unit when the first receive coil 171 (namely, a receive coil coupled to the table 120 and determined relative to a position of the table 120) is used is described above. An example of automatically selecting a coil and a coil unit when a second receive coil 172 is used will be further described in the following example. The second receive coil 172 may be a receive coil disposed on the body of the scan subject 16, and also includes a plurality of coil units 1721 arranged in a matrix. According to different imaging requirements, the second receive coil may be attached to one side of the body of the scan subject 16 in a tiling/covering manner, or may surround/wrap a part of the body of the scan subject 16. In the former manner, the second receive coil generally covers an upper side (a side away from the table 120) of the scan subject, and the second receive coil is used in combination with the first receive coil to obtain imaging data of the scan subject during scanning. In the latter manner, only the second receive coil may be used to obtain imaging data, and the first receive coil does not need to be used, but a doctor or a technician sometimes inputs information inconsistent with the actual coupling manner of coil during setting. For example, the second surface coil is tiled, and if the doctor or the technician sets as only using the second surface coil, obtained imaging data is incomplete, the quality of a reconstructed image is severely affected, and a scanning process usually needs to be performed again.

In the example of this embodiment, the processing device 1520 may identify, based on the three-dimensional image captured by the 3D camera 1510, a coupling manner in which the second receive coil 172 is coupled to the scan subject 16, and select all or one of the first receive coil 171 and the second receive coil 172 based on the coupling manner in which the second receive coil 172 is coupled to the scan subject 16. The control device 1530 is configured to turn on the coil selected from the first receive coil 171 and the second receive coil 172, which may be specifically implemented by controlling switching of the first receive coil and the second receive coil. For example, when the second receive coil 172 is coupled to the scan subject in a tiling manner, the first receive coil and the second receive coil may be selected to be turned on; and when the second receive coil 172 is coupled to the scan subject in a surrounding manner, only the second receive coil may be selected to be turned on.

In the example of this embodiment, when the second receive coil is selected, the processing device 1520 further determines relative position information of the part 162 of interest of the scan subject 16 and the second receive coil 172 based on the three-dimensional image captured by the 3D camera 1510, and determine a coil unit 1721 required to be turned on in the second receive coil 172 based on the relative position information of the part 162 of interest of the scan subject 16 and the second receive coil 172. Similarly, a coil unit 1721 closer to the region 163 of interest of the scan subject 16 can be determined.

Seventh Embodiment

Figure 16:
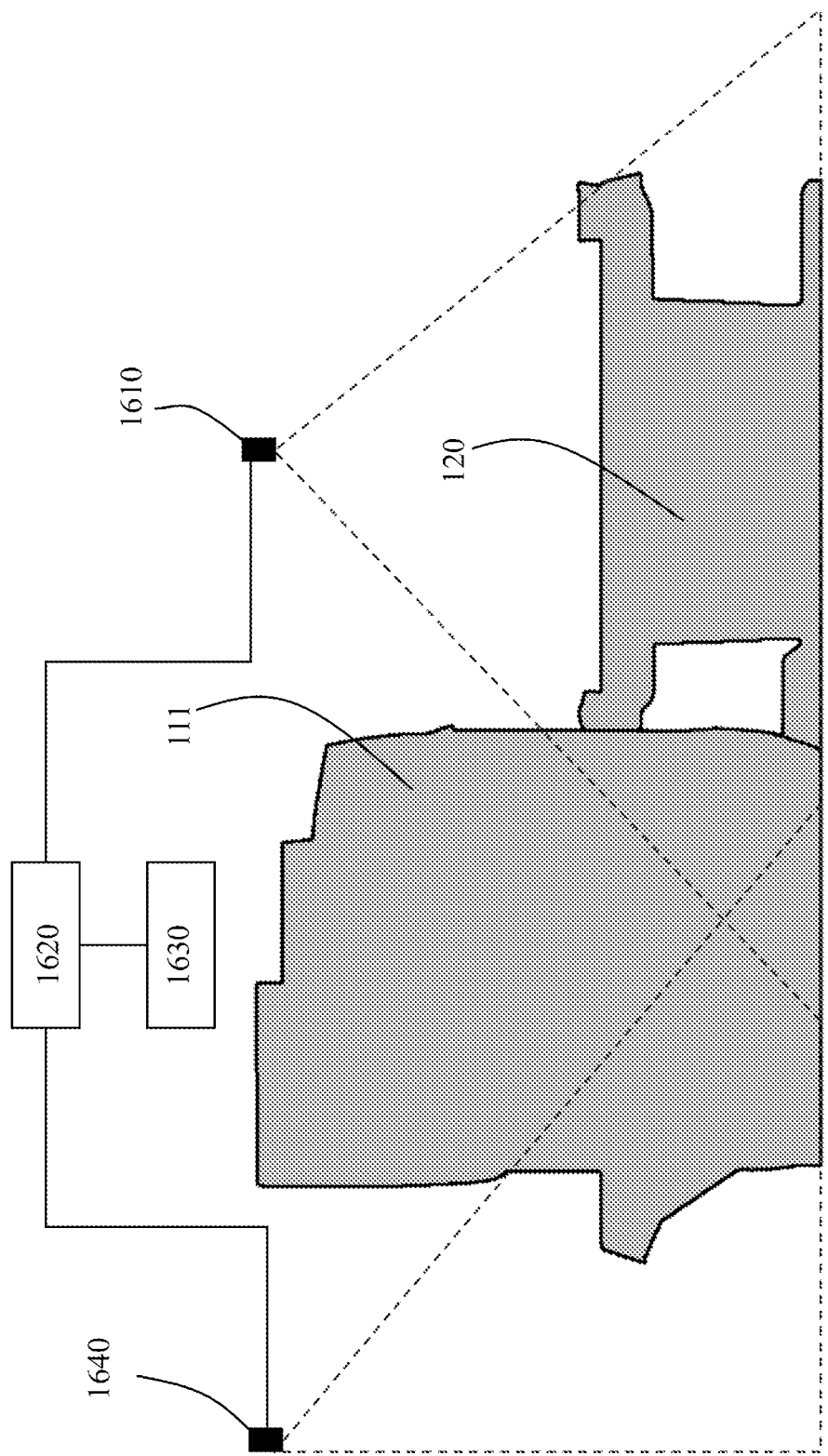
FIG. 16 shows a schematic structural diagram of a scanning control system according to another embodiment of the present invention.

FIG. 16 shows a schematic structural diagram of a scanning control system according to another embodiment of the present invention. The scanning control system may be coupled to the magnetic resonance imaging system shown in FIG. 1. The scanning control system may include a 3D camera 1610, a processing device 1620, and a control device 1630.

The 3D camera 1610 may be the same apparatus as the 3D cameras 210, 310, 410, 710, 1310, 1510 or an apparatus mounted and disposed in a similar manner.

The 3D camera 1610 is configured to photograph the second region 102 to obtain a first environment image before a scanning process starts or after the scanning process ends. As described above, the second region 102 includes a positioning region of the table 120.

The processing device 1620 is configured to compare the first environment image with a prestored standard environment image, and indicate a maintenance state based on a comparison result. The aforementioned standard environment image displays an on-site environment of the first region in a normal maintenance state, for example, may include relative positions of various components, postures, and the like in the second region. If no scanning task is currently executed, on-site maintenance may be performed, and upon completion of the maintenance, a current image captured by the 3D camera 1610 may be compared with the standard environment image to determine whether the maintenance is improper. For example, when it is found that placement or posture errors exist in the current image, or redundant parts, components, or things exist as compared with the standard environment image, it indicates that the maintenance state is abnormal. At this time, the control device 1630 may be used to control, for example, a sound production apparatus, a display apparatus, or a light emitting apparatus, of the magnetic resonance imaging system to issue a corresponding warning. If the current image is consistent with the standard environment image, it indicates that the maintenance state is normal.

With reference to FIG. 1 and FIG. 16 in combination, similarly, the 3D camera 1640 may further be used to photograph the third region 103 to obtain a second environment image, and the second environment image is compared with another prestored standard image, and a maintenance state is indicated based on a comparison result.

Figure 17:
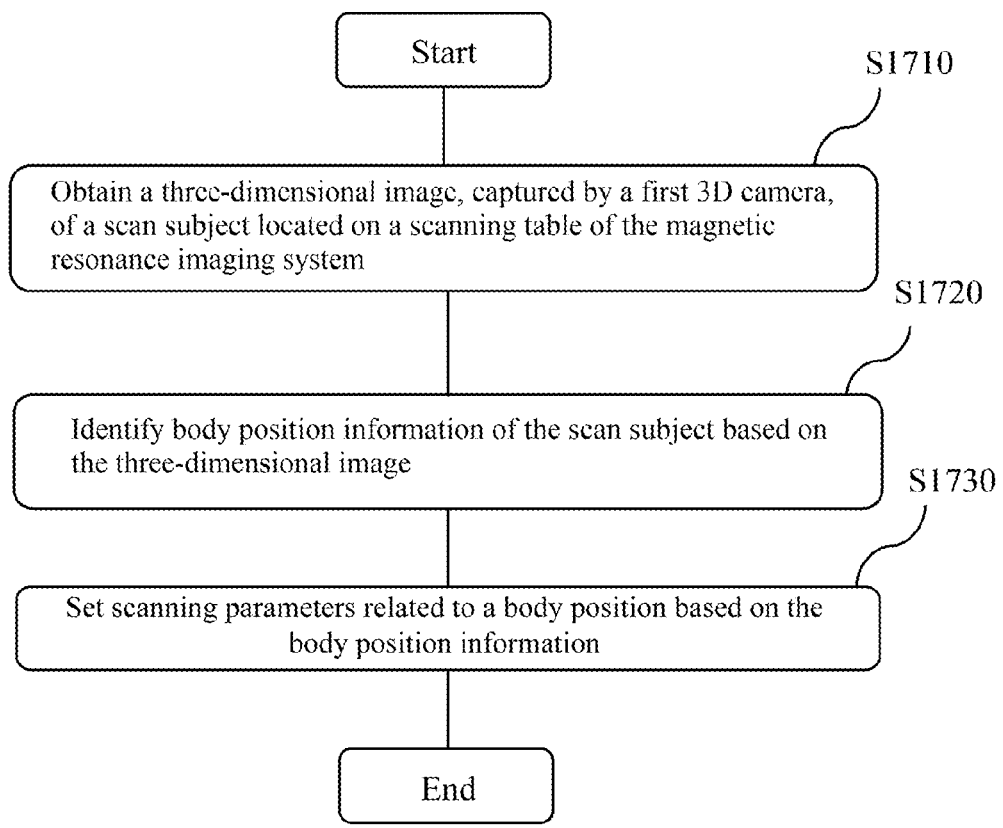
FIG. 17 and FIG. 18 respectively show flowcharts of a scanning control method for a magnetic resonance imaging system according to one embodiment of the present invention.
Figure 18:
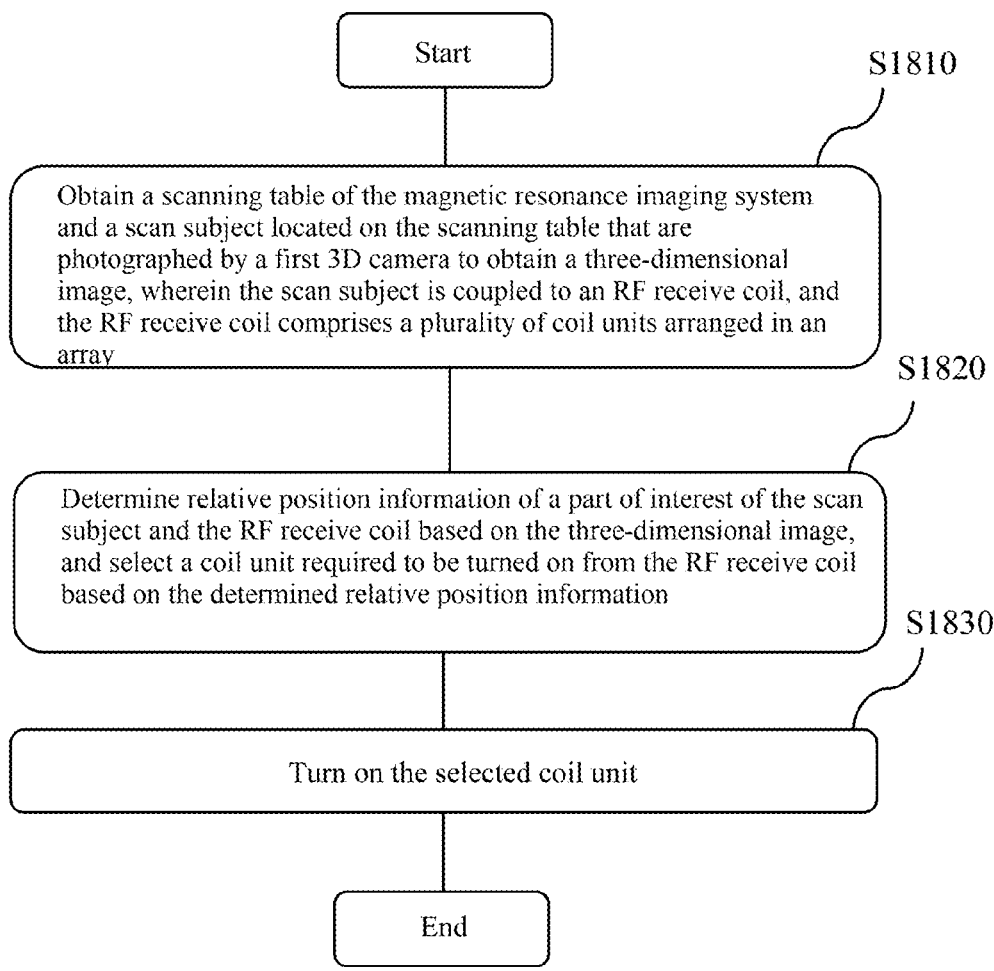

FIG. 17 and FIG. 18 respectively show flowcharts of a scanning control method for a magnetic resonance imaging system according to one embodiment.

As shown in FIG. 17, the method includes steps S1710 to 1730.

In step S1710, a three-dimensional image, captured by a first 3D camera, of a scan subject located on a scanning table (for example, the table 120) of the magnetic resonance imaging system is obtained.

In step S1720, body position information of the scan subject is identified based on the three-dimensional image.

In step S1730, scanning parameters related to a body position is set based on the body position information.

Optionally, the method may further include: determining, based on the body position of the scan subject displayed in the three-dimensional image, a slice position and angle for image reconstruction, and sending the determined slice position and angle to an image reconstruction unit of the magnetic resonance imaging system.

As shown in FIG. 18, the method includes steps S1810 to S1830.

In step S1810, a scanning table of the magnetic resonance imaging system and a scan subject located on the scanning table that are photographed by a first 3D camera is obtained to obtain a three-dimensional image, wherein the scan subject is coupled to an RF receive coil (for example, the first receive coil 171 and the second receive coil 172), and the RF receive coil includes a plurality of coil units (for example, the coil units 1711 and 1721) arranged in an array.

In step S1820, relative position information of a part of interest of the scan subject and the RF receive coil is determined based on the three-dimensional image, and a coil unit required to be turned on is selected from the RF receive coil based on the determined relative position information.

In step S1830, the selected coil unit is turned on.

The method may further include: identifying, based on the three-dimensional image, a coupling manner in which the second receive coil is coupled to the scan subject, and selecting all or one of the first receive coil and the second receive coil based on the coupling manner in which the second receive coil is coupled to the scan subject; and turning on the coil selected from the first receive coil and the second receive coil.

When the first receive coil is selected, a required coil unit is selected from the first receive coil based on relative position information of the part of interest of the scan subject and the first receive coil. When the second receive coil is selected, a required coil unit is selected from the second receive coil based on relative position information of the part of interest of the scan subject and the second receive coil.

The method may further include:
  obtaining, before a scanning process starts or after the scanning process ends, a first environment image of a first region that is photographed by the first 3D camera;
  comparing the first environment image with a prestored first standard environment image; and
  indicating a maintenance state of the magnetic resonance imaging system based on a comparison result of the first environment image and the first standard environment image.

The method may further include:
  obtaining, before the scanning process starts or after the scanning process ends, a second environment image of a third region (for example, third region 103) that is captured by a second 3D camera, wherein the first 3D camera and the second 3D camera are respectively located on two sides of a magnet assembly of the magnetic resonance imaging system, and the third region comprises a region located outside a scanning chamber of the magnetic resonance imaging system and opposite to a rear end of the scanning chamber;
  comparing the third environment image with a prestored second standard environment image; and
  indicating the maintenance state of the magnetic resonance imaging system based on a comparison result of the third environment image and the second standard environment image.

The above embodiments describe that a 3D camera is used to capture images of different regions of a magnetic resonance scanning room, various analyses are performed on these images and a magnetic resonance imaging system is automatically controlled based on analysis results, so that pre-scanning and scanning processes of magnetic resonance imaging can be performed more precisely and efficiently. For example, a positioning guidance mark is more precisely indicated to achieve precise and rapid patient positioning; a positioning state of a receive coil is indicated to help an operator arrange a surface receive coil more rapidly and accurately; a matching state of the receive coil and a part of interest is indicated to avoid image quality problems caused by position mismatch; the moving speed of a scanning table is estimated so as to ensure patient safety while rapidly moving the patient; a body position is automatically detected to avoid resource waste and image quality problems caused by errors in setting the body position, and more precise body position information enables reconstruction of images better reflecting patient lesions; a coupling manner in which a coil is coupled to a subject is automatically detected to automatically select a coil, and a coil unit is automatically selected according to the relative position of the coil and the part of interest, so as to avoid resource waste and image quality problems caused by errors in selecting the coil and the coil unit; an actual patient image and a standard human body structure image are used in combination to achieve rapid selection of a region of interest.

The following embodiment will describe one example of implementing magnetic resonance imaging using various embodiments of the present invention, wherein after a previous imaging process ends, a current imaging process is started based on a user operation, and pre-scanning is performed:
  a lens of a 3D camera is controlled to focus on a first region. The 3D camera may be controlled to photograph a patient in the first region based on a user operation, or the 3D camera may be used to monitor whether there is a patient in position in the first region, and if yes, a first three-dimensional image is automatically obtained, and a positioning mark is projected on the table 120 based on an analysis of the first three-dimensional image, and the table 120 is adjusted to a height adapted to the patient.

The lens of the 3D camera is focused on the region where the table 120 is located automatically or based on the user operation.

The patient sits at the positioning mark and is then positioned on the table 120 according to body position requirements.

The 3D camera is used to photograph the patient on the table 120 to obtain a second three-dimensional image, and the second three-dimensional image is used in combination with a prestored standard human body image to automatically determine and select a region of interest. This step may be performed in place of positioning scanning, or performed in combination with positioning scanning.

It is determined whether a part to be scanned (a part of interest) of the patient is positioned at an appropriate position based on an analysis of the second three-dimensional image, and if not, the operator or the patient is informed until the part of interest is positioned properly.

After a surface coil is used to cover or surround a body part of the patient, the 3D camera is controlled to capture a third three-dimensional image based on an operation of the operator or an automatic monitoring result, wherein the third three-dimensional image includes the table, the patient, and the surface coil on the body of the patient. It is determined whether the surface coil is positioned opposite to the part of interest based on an analysis of the third three-dimensional image, and if not, the operator is informed until the surface coil is positioned properly.

A current relative position of the head of the patient is determined based on the second three-dimensional image, the third three-dimensional image, or another three-dimensional image obtained by photographing the patient on the table 120 by the 3D camera, and moving speeds of the patient at different travels in a traveling direction thereof (Z direction) are estimated according to the relative position of the head.

Scanning is performed:
  a body position of the patient is determined based on an analysis of the third three-dimensional image and parameters related to the body position are automatically set.

A coupling manner in which the surface coil is coupled to the patient is determined based on the analysis of the third three-dimensional image. For example, if in a covering manner, the surface coil and the receive coil disposed in the table 120 are selected to be turned on; and if in a surrounding manner, only the surface coil is selected to be turned on.

A coil unit is further selected from the selected coil based on the analysis of the third three-dimensional image.

The table 120 is controlled to move at the estimated speed, so as to position the part of interest of the patient at a preset position, for example, opposite to a scanning center.

Image data during scanning is obtained through the selected coil unit, and a reconstruction unit performs image reconstruction based on the image data, wherein a slice angle and position are selected according to the body position information.

The table 120 is controlled to move at the estimated speed, so as to move the patient out of the scanning chamber 116.

The imaging process ends.

The order of describing the steps in the above example is not intended to limit the actual order of execution, and there are a plurality of variable embodiments to complete the imaging process.

In various embodiments above, the processing unit and the control unit include a circuit that is configured to execute one or a plurality of tasks, functions or steps discussed herein. In various embodiments, the processing unit may be integrated with the data processing unit 120 of the magnetic resonance imaging system, and the control unit may be integrated with the control unit 130 of the magnetic resonance imaging system. The "processing unit" and "control unit" used herein are not intended to necessarily be limited to a single processor or computer. For example, the processing unit and the control unit may include a plurality of processors, ASICs, FPGAs and/or computers, and the plurality of processors, ASICs, FPGAs and/or computers may be integrated in a common housing or unit, or may be distributed among various units or housings. The depicted processing unit and control unit include a memory. The memory 130 may include one or more computer-readable storage media. For example, the memory 130 may store information about system characteristics (for example, information about spatial gradients), images (for example, standard human body images), algorithms or processes for performing any of the embodiments described above, and the like. Further, the process flow and/or flowchart (or aspects thereof) discussed herein may represent one or more instruction sets stored in the memory for guiding scanning control or pre-scanning control.

As used herein, an element or step described as singular and preceded by the word "a" or "an" should be understood as not excluding such element or step being plural, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements that do not have such property. The terms "including" and "in which" are used as the plain-language equivalents of the respective terms "comprising" and "wherein." Furthermore, in the appended claims, the terms "first", "second," "third" and so on are used merely as labels, and are not intended to impose numerical requirements or a particular positional order on their objects.

This written description uses examples to disclose the present invention, including the best mode, and also to enable those of ordinary skill in the relevant art to implement the present invention, including making and using any devices or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements without substantial differences from the literal language of the claims.

What is claimed is:

1. A scanning control system for a magnetic resonance imaging system, comprising:
   a first three-dimensional (3D) camera configured to capture a three-dimensional image of a scan subject located on a scanning table of the magnetic resonance imaging system;
   processing circuitry configured to identify body position information of the scan subject based on the three-dimensional image;
   control circuitry configured to set scanning parameters related to a body position of the scan subject based on the identified body position information; and
   wherein the processing circuitry is further configured to determine, based on the body position of the scan subject displayed in the three-dimensional image, a slice position and angle of image data acquired via a scan by the magnetic resonance imaging system for image reconstruction, and to send the determined sliced position and angle of the image data for an image reconstruction unit of the magnetic resonance imaging system for the image reconstruction to generate an image of a region of the scan subject based on the image data;
   wherein the first 3D camera is further configured to photograph a first region to obtain a first environment image before a scanning process starts or after the scanning process ends, wherein the first region comprises a positioning region of the scanning table;
   the processing circuitry is configured to compare the first environment image with a prestored first standard environment image; and
   the control circuitry is configured to indicate a maintenance state of the magnetic resonance imaging system based on a comparison result of the first environment image and the prestored first standard environment image;
   further comprising:
   a second three-dimensional (3D) camera configured to photograph a second region to obtain a second environment image before the scanning process starts or after the scanning process ends, wherein the first 3D camera and the second 3D camera are respectively located on two sides of a magnet assembly of the magnetic resonance imaging system, and the second region comprises a region located outside a scanning chamber of the magnetic resonance imaging system and opposite to a rear end of the scanning chamber;
   the processing circuitry is further configured to compare the second environment image with a prestored second standard environment image; and
   the control circuitry is further configured to indicate the maintenance state of the magnetic resonance imaging system based on a comparison result of the second environment image and the prestored second standard environment image.

2. A scanning control method for a magnetic resonance imaging system, comprising:

obtaining a three-dimensional image, captured by a first three-dimensional (3D) camera, of a scan subject located on a scanning table of the magnetic resonance imaging system;
identifying body position information of the scan subject based on the three-dimensional image;
setting scanning parameters related to a body position of the scan subject based on the identified body position information;
determining, based on the body position of the scan subject displayed in the three-dimensional image, a slice position and angle of image data acquired via a scan by the magnetic resonance imaging system for image reconstruction; and
sending the determined slice position and angle of the image data to an image reconstruction unit of the magnetic resonance imaging system for the image reconstruction to generate an image of a region of the scan subject based on the image data;
wherein the first 3D camera is further configured to photograph a first region to obtain a first environment image before a scanning process starts or after the scanning process ends, wherein the first region comprises a positioning region of the scanning table;
comparing the first environment image with a prestored first standard environment image; and
indicating a maintenance state of the magnetic resonance imaging system based on a comparison result of the first environment image and the prestored first standard environment image;
further comprising:
a second three-dimensional (3D) camera configured to photograph a second region to obtain a second environment image before the scanning process starts or after the scanning process ends, wherein the first 3D camera and the second 3D camera are respectively located on two sides of a magnet assembly of the magnetic resonance imaging system, and the second region comprises a region located outside a scanning chamber of the magnetic resonance imaging system and opposite to a rear end of the scanning chamber;
comparing the second environment image with a prestored second standard environment image; and
indicating the maintenance state of the magnetic resonance imaging system based on a comparison result of the second environment image and the prestored second standard environment image.

* * * * *